(12) United States Patent
Wiedenbein

(10) Patent No.: US 10,398,446 B2
(45) Date of Patent: Sep. 3, 2019

(54) SURGICAL INSTRUMENT

(71) Applicant: Cardiomedical GmbH, Langenhagen (DE)

(72) Inventor: Wolfgang Wiedenbein, Seelze (DE)

(73) Assignee: Cardiomedical GMBH, Langenhagen (DE)

( * ) Notice: Subject to any disclaimer, the term of this patent is extended or adjusted under 35 U.S.C. 154(b) by 340 days.

(21) Appl. No.: 14/874,515

(22) Filed: Oct. 5, 2015

(65) Prior Publication Data

US 2016/0100841 A1    Apr. 14, 2016

(30) Foreign Application Priority Data

Oct. 9, 2014  (DE) .................. 10 2014 014 733

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 17/128* (2013.01);
(Continued)

(58) Field of Classification Search
CPC ........ A61B 17/122; A61B 2017/00473; A61B 2017/2931; A61B 2017/294;
(Continued)

(56) References Cited

U.S. PATENT DOCUMENTS

| | | | |
|---|---|---|---|
| 1,817,988 A * | 8/1931 | Klamt | ....................... B25B 7/12 81/315 |
| 6,036,706 A | 3/2000 | Morejohn et al. | |
| 2005/0251183 A1* | 11/2005 | Buckman | ............... A61B 17/08 606/157 |
| 2008/0234725 A1* | 9/2008 | Griffiths | ................. A61B 17/29 606/208 |

(Continued)

FOREIGN PATENT DOCUMENTS

| | | |
|---|---|---|
| DE | 7139469 U | 2/1973 |
| DE | 4412171 A1 | 10/1995 |

(Continued)

OTHER PUBLICATIONS

European Search Report dated Jan. 12, 2016, issued in the corresponding European application.

*Primary Examiner* — David C Eastwood
(74) *Attorney, Agent, or Firm* — Husch Blackwell LLP

(57) ABSTRACT

A surgical instrument with a parallel gripping and clamping vascular clamp, which is equipped with coupling elements which makes possible a combination of a known detachable operating arrangement and of an actuating tool, in order to keep the access opening in the thorax free of intrusive instruments. With the parallel gripping and clamping operating means of the inventive vascular clamp, the known scissor-like means are dispensed with, and a parallel adjustment of the operating means takes place by means of a lever gear according to the invention. The lever gear is formed from a stationary lever, constructed as a body element, and from several movable levers, consisting of the tension- and pressure element, a push-pull rod, two toggle levers, two pivot arms and two movable branches. The lever gear has nine axes and converts a linear drive movement for adjusting the operating means into a rotationally movable one, whereby the two movable branches are displaceable sub- (Continued)

stantially in a parallel manner towards one another and away from one another.

4 Claims, 3 Drawing Sheets

(51) Int. Cl.
    *A61B 17/00*         (2006.01)
    *A61B 17/29*         (2006.01)

(52) U.S. Cl.
    CPC ............... *A61B 2017/00473* (2013.01); *A61B 2017/294* (2013.01); *A61B 2017/2931* (2013.01); *A61B 2017/2941* (2013.01); *A61B 2017/2944* (2013.01); *A61B 2017/2946* (2013.01)

(58) Field of Classification Search
    CPC .... A61B 2017/2941; A61B 2017/2944; A61B 2017/2946; A61B 17/128; A61B 17/1285; A61B 2017/2939; A61B 2017/2927; A61B 2017/2932; A61B 2017/2933; A61B 2017/2938; A61B 2017/2947; A61B 17/28; A61B 17/2804; A61B 2017/2808; A61B 2017/2926; B25B 7/123; B25B 7/12; B25B 7/18
    See application file for complete search history.

(56) References Cited

U.S. PATENT DOCUMENTS

2008/0287995 A1* 11/2008 Gauthier .............. A61B 17/025
                                              606/246
2014/0107697 A1* 4/2014 Patani .................... A61B 17/12
                                              606/208

FOREIGN PATENT DOCUMENTS

| DE | 19719090 A1 | 11/1998 |
| DE | 60211044 T2 | 4/2007 |
| DE | 60224460 T2 | 12/2008 |
| EP | 1878390 A1 | 1/2008 |
| EP | 2335609 B1 | 4/2012 |
| WO | 2008/115288 A1 | 9/2008 |
| WO | 2009/064807 A1 | 5/2009 |
| WO | 2013/003256 A2 | 1/2013 |

* cited by examiner

SURGICAL INSTRUMENT

CROSS REFERENCE

This application claims priority to German Application No. 10 2014 014733.9, filed Oct. 9, 2014, the entirety of which is hereby incorporated by reference.

FIELD OF TECHNOLOGY

The present invention relates generally to the field of medicine, in particular surgery.

BACKGROUND

In the surgical field, instruments, devices or methods are used in order to examine the interior of living organisms and/or to use for operative interventions. Among the surgical instruments are all medical instruments which are principally used in surgery. This also includes surgical instruments for the ligation or other alternative compression of duct- or tube-shaped body parts, preferably of blood vessels. Such surgical instruments are associated with the range of gripping or respectively clamping instruments and are available in a great variety of types and are sufficiently known. Gripping or respectively clamping surgical instruments are used for example in interventions in cardiac, thoracic and vascular surgery. In cardiac and thoracic surgery, usually an open operation is carried out in which, by opening up the thorax, access to the heart is created. The access takes place generally by means of a median sternotomy, wherein for opening the ribcage a longitudinal incision, approximately 25 cm long, is produced through the breastbone. In thoracotomy, the surgical opening of the thorax takes place by an intercostal incision, i.e. by a small incision into the intercostal space. The opening produced by the sternotomy or thoracotomy is held free by a rib retractor, which is used for expanding the ribcage and keeping it open. The opening serves as an access for the surgeon for operative interventions. The interventions on the organic body parts then take place by means of a plurality of different surgical instruments through the opening which has been produced in the ribcage. If, for example, the heart of the patient is exposed, various catheters, cannulas and clamps are applied directly onto the heart and the large blood vessels. Typically, the aorta is occluded with a vascular clamp around the ascending aorta, in order to isolate the coronary arteries from the remainder of the arterial system, wherein here occluding is understood to mean the gripping, compressing, clamping and holding of a vessel. The surgical instruments which are necessarily used reduce the body opening and therefore impede the activity of the surgeon in his field of vision. In addition, owing to the size of the opening, the tissue damage which has occurred and the operative trauma, a quick healing process is not to be expected in the patient.

Medical instruments of this type are known from the prior art. In particular, the gripping and clamping surgical instruments in the various types of construction and embodiments have proved to be successful as surgical instruments in many cases in operative interventions. These instruments have the advantage that the jaw parts or respectively the branches distribute the closing pressure in any desired position uniformly over the width of the vessels which are to be clamped.

DE 7139469 already shows a vascular clamp with two branch parts connected to one another in a pivotally movable manner about an axis. These branch parts are movable by pivotal movements for the closing and opening of the jaw, in a direction facing one another or respectively facing away from one another. By the connection of the jaw parts with the branch parts via a known parallel guide, it is achieved that the jaw parts, on the movement of the branch parts in a direction facing one another, or away from one another, are always moved parallel to one another, wherein the jaw parts are detachably connected with the branch parts. The parallel guide is constructed such that each jaw part with a branch part is pivotable about an axis lying on the side of the pivot axis of the branch parts facing away from the grips of the branch parts and at a distance therefrom, and is connected with the other branch part on the side of the pivot axis of the branch parts facing the grips of the branch parts and at a distance therefrom by means of a pin guided in a slot. This vascular clamp concerns a so-called opening and closing scissor-shaped clamping forceps. Such a clamping forceps consists basically of three regions, an operating means, a shaft part and a handling part. The lever mechanism of the vascular clamp consists in that, when the branch parts are moved towards one another or away from one another, the jaw parts are then moved towards one another by a path length corresponding to the reduction of the parallel guide, wherein the jaw parts always remain in their position parallel to one another. This embodiment of a vascular clamp does not, however, fulfil the requirements placed on it from minimally invasive surgery. On the one hand, a continuous adjustment of the jaw parts is absent, whereby a uniform clamping can be made possible with as little traumization of the tissue as possible, and on the other hand the embodiment does not correspond to that of a space-saving type of construction, which promotes an operative intervention in the access to the interior of the body. A separation of the vascular clamp into several components or respectively an ability of the vascular clamp to be dismantled between the jaw parts and the branch parts during the operation is not possible.

A further development of the above-mentioned vascular clamp, in particular for endoscopy, is disclosed in the prior art by DE 44 12 171 A1. In this embodiment, the movable jaw part is connected via a parallelogram-like articulated connection with the holder, which is formed in a fork-shape. Both jaw parts are moved continuously from an opened and/or closed position of use, parallel to the longitudinal axis of the holder. In addition, the front jaw joints and rear jaw joints are connected with a holder. Here, the front jaw joints have a shared axis via a front articulation- and retaining axis, close to the end of the holder, wherein both front jaw joints overlap one another. Furthermore, the front jaw joints, on closing of the jaw parts, can dip into the latter. The rear jaw joints are fastened on the holder jointly via a rear articulation axis, wherein the articulation axis is displaceable. Here, the rear articulation axis is provided with an opening for guiding through a tension- and pressure element, wherein the rear jaw joint engages into a groove by means of a rear jaw articulation axis. Proceeding from a hand grip, a tension- and pressure element runs through a sleeve-shaped operating element into the holder and terminates there at a rod articulation axis. The rod articulation axis is guided in a slot of the holder and is connected via tension- and pressure elements with the lever-shaped front jaw joints. The lever mechanism of the vascular clamp consists in that the front and rear jaw joints can be displaced in the manner of a parallelogram in the grooves of the jaw parts and in the groove of the fork-shaped holder, wherein the jaw joints on the one hand, on closing of the jaw parts, dip between the forks of the holder, and on the other hand into the jaw parts. By a movement of the tension- and pressure element, a displacement of the rod articulation axis takes place into a slot of the holder, whereby the jaw parts open or close. The parallelogram-like and continuous adjustment of this vascular clamp is regarded as obvious prior art. A disadvantage in this embodiment of an endoscopic instrument is the non-space-saving type of construction, which does not promote an operative intervening in the access to the interior of the body and does not reduce the number of instruments lying in the body opening. This means that the ability of the surgical instrument to be dismantled does not exist during usage, because a separation of the jaw part (operating instrument) from the holder (shaft part and handling part) is not possible during the operation.

The ability of a surgical instrument to be dismantled is disclosed in DE 197 19 090 A1. The concern here is with a minimally invasive surgical instrument which is able to be dismantled with jaw parts (branches) forming an operating instrument (operating means) for the gripping, holding and/or clamping of organs for surgical minimally invasive interventions, wherein the jaw parts, for closing and opening the operating instrument, are movable in a parallel manner towards one another and away from one another. The moving of the jaw parts in a parallel manner towards one another and away from one another takes place via two pairs of cranks respectively comprising an outer crank and an inner crank, which form an antiparallel crank gear in the form of a so-called double parallelogram linkage. A rotary movement of a worm gear is implemented by a translatory movement of the crank gear, wherein to carry out the parallel displacement of the jaw parts, the crank gear or a sliding block guide and a push- and pull element connected therewith is used. This instrument is able to be dismantled during use or respectively during the operation. To carry out the capability of being dismantled, the operating instrument (operating means) and the carrier instrument (shaft part) comprise coupling means which interact, wherein the coupling means form a coupling connection, also detachable during the use of the instrument, between the operating instrument (operating means) and the carrier instrument (shaft part). The coupling means comprise a push shaft and an instrument insert, see Claim 11 in this respect. The disadvantage of the instrument is to be found during handling. The disadvantage consists in the coupling ability of the coupling means during the use of the operating instrument (operating means) to separate the latter from the instrument shaft (carrier instrument) and to bring them together again. To produce the connection between the operating instrument and the instrument shaft or respectively carrier instrument, the centre axis of the operating instrument and the centre axis of the carrier instrument must be aligned with one another. This is as good as never the case during the operative use, because the vessels are relatively soft and movable, whereby the operating instrument and therefore its centre axis take up a position which does not coincide with the centre axis of the introduced carrier instrument. Furthermore, it is disadvantageous that the production of such an operating instrument, of such a carrier instrument and of such an instrument grip, is very sophisticated owing to the technical complexity, whereby the production costs of the entire instrument are too high. These high production costs can also be explained by the multiplicity of the required individual parts of the instrument. A further disadvantage consists in that the multiplicity of individual small parts can lead to be clamp having cavities, recesses etc., which can easily become contaminated during the use of the instrument in an operation, whereby the functioning of the instrument is impaired and safety can no longer be guaranteed.

A further surgical clamping system with a clamp, which has two jaw parts, which can be opened and closed reciprocally parallel to one another, and which are able to be actuated relative to one another from a completely open position into a completely closed position and have a detachable supply- and removal device with a bayonet connection, can be seen from DE 602 11 044 T2 an DE 602 24 460 T2. The introducing or removing of the clamp from the interior of the body takes place via an actuating member which cooperates with the supply- and removal device, wherein the clamp has a screw/nut drive or a worm drive, which are in engagement with the proximal ends of the jaw parts. In the screw/nut drive, the screw is coupled permanently with a push-pull rod which is in engagement with the jaw part by means of a joint. A rotating of the nut brings about an axial displacement of the screw, which pushes or pulls the push-pull rod. If the nut is replaced by a worm drive and the screw is replaced by a toothed rack, the gear system is a worm gear. In these instruments, as in the previously mentioned instrument from DE 197 19 090 A1, the coupling ability of the coupling means to separate an operating instrument from the instrument shaft during use and to receive it with this again is also beset with substantial disadvantages. The disadvantages consist in the handling of the instrument which result from the technical embodiment of the bayonet connection. To produce the connection between the operating instrument and the instrument shaft or respectively carrier instrument, the centre axis of the operating instrument and the centre axis of the carrier instrument must be aligned with one another. However, this does not exist during the operative use, and in the removal, because the clamp used in the interior of the body takes up a position in which the centre axis of the operating instrument does not coincide with the centre axis of the carrier instrument. It can be seen how complicated the removal of a clamp is from the following description. When the introduced clamp is no longer required, the supply- and removal device can be introduced again into the site of the operation, and with the use of an additional gripping means the clamp is held so as to be immobile. The distal end of the hollow shaft is then slipped over the proximal end of the clamp, and the handle is simultaneously pressed and rotated, so that the bayonet pins come into engagement with the bayonet. Whilst the handle is being held, the actuating member is introduced into the proximal end of the handle and guided through the hollow shaft and simultaneously rotated in the hollow shaft until the distal end penetrates into the slot of the nut and comes into engagement therewith, at which moment the detent comes into engagement with the groove and locks the actuating member in situ. The button is then rotated, whilst the handle is held immobile, in order to open the jaw part of the clamp. The clamp can now be removed from the tissue. From this description, the complex handling can be seen which is necessary to remove a clamp, and which is only possible with an additional instrument (gripping means), which holds the clamp immobile, so that the supply- and removal device can be connected with the clamp. A further disadvantage of the clamp consists in that in the case of the small parts of the worm gear, it can lead to the cavities, recesses, teeth etc. easily being able to be become contaminated, whereby the functioning of the instrument is impaired and the safety during a use of the instrument in an operation can no longer be guaranteed. A further disadvantage consists in the technical embodiment of the surgical clamp, which entails high costs in production.

EP 2 335 609 A1 is regarded as the nearest prior art in the continuous adjustment of a jaw part and the ability of a surgical instrument to be dismantled. EP 2 335 609 B1 discloses a surgical instrument which is able to be dismantled and completed. The surgical instrument which is able to be dismantled comprises a vascular clamp consisting of an operating instrument (operating means) with two branches, a supply- and removal device as carrier instrument, which consists of an operating arrangement and an actuating tool (handling part) with an instrument grip. This surgical instrument, owing to its simple ability to be dismantled during use or respectively during the operation, is used in minimally invasive surgery. The vascular clamp is gripped by means of a simply detachable operating arrangement, wherein an actuating tool, able to be pushed in and out, can open and close the movable branch of the operating means. For this, the vascular clamp contains a coupling arrangement and a continuous adjusting arrangement. For gripping or respectively receiving, and for releasing or respectively separating the vascular clamp from the operating arrangement (carrier instrument), the operating arrangement contains a gripping arrangement and has a fixing device, whereby a detachable connection between the vascular clamp and the operating arrangement can be produced in a simple manner. The coupling arrangement and the gripping arrangement form the coupling means which interact, wherein the coupling means form a coupling connection between the operating instrument (operating means) and the operating arrangement (the carrier instrument) which is also able to be detached during the use of the instrument. The actuating tool (handling part) with instrument grip engages into the adjusting arrangement of the vascular clamp for the continuous opening and closing of the branch. The disadvantage of this embodiment of the minimally invasive surgical instrument consists in that the jaw parts (branches) forming for the closing and opening of the operating instrument (operating means) are not movable in a parallel manner towards one another and away from one another, but rather operate according to the functional principle of a scissors, whereby a uniform gripping, holding and/or clamping of organs for surgical minimally invasive interventions is not possible.

SUMMARY OF THE INVENTION

In order to fulfil the requirements set for the surgical instruments from minimally invasive surgery, it is necessary to develop new embodiments of surgical instruments.

It is desired to create a medical instrument of the type named in the introduction for use in minimally invasive surgery, which avoids the above-mentioned disadvantages and shortcomings of the known arrangements. Accordingly, it is an object of the present invention to provide a technical solution for a surgical vascular clamp which on the one hand is simple and cost-effective to produce, and on the other hand also makes it possible to produce a surgical instrument for the increased requirements which is equipped with a simple functional geometry from an ergonomic and handling point of view. This surgical vascular clamp is not only to grip and clamp organic body parts in a particularly uniform manner, but the surgeon is also to be given the possibility of being able to set a different clamping force. The differently adjustable clamping force is to correspond to various medical applications. Such a minimally invasive surgical instrument is also designated as an MIC instrument and is to have some positive characteristics of the known surgical clamps of the prior art.

A further object consists in making possible the characteristics of the simple ability of an instrument to be dismantled and the secure gripping of an operating instrument (operating means) by an operating arrangement (carrier instrument), as known from EP 2 335 609 B1. Furthermore, both jaw parts, hereinafter designated as branches, are to be continuously adjustable and arrestable on the operating instrument (operating means), hereinafter designated as vascular clamp. The two branches of the vascular clamp are to be suited, parallel to one another, as e.g. known from DE 44 12 171 A1, DE 197 19 090 A1 and DE 602 24 460 T2, for the opening and closing of an operating means, and are to enable a uniform clamping with as little traumatization to the tissue as possible. In addition, they are to run substantially parallel to one another in any desired position between the completely open and the completely closed position.

As a further object, a lever gear is to be used in order to fulfil the technical requirements of the ability to be dismantled and the parallel adjustment of branches, for the opening and closing of an operating means. An instrument is also to be considered from the point of view of cleaning and disinfecting. Therefore, the design and the reduction of the multiplicity of individual components in an instrument play an important role. Such a surgical instrument, which is able to be dismantled, would have an advantageous handling and, owing to its ability to be dismantled, would not impair the operation field or respectively the field of vision of the operator and therefore the access opening in the thorax. Access openings typically have the smallest possible diameter, which corresponds to the philosophy of minimally invasive surgery. On the basis of these specifications, as far as possible no other instruments are to reduce the access opening. However, this can only be guaranteed when the instruments are able to be dismantled.

In order to produce a surgical instrument equipped with these features of the present invention, in particular a minimally invasive surgical vascular clamp, for use in operative interventions on the human or animal body in minimally invasive surgery, it is proposed according to the invention to configure the surgical instrument such that an ergonomically configured supply- and removal device is made available for the surgeon, consisting of an operating arrangement and an actuating tool with instrument grip for the adjusting of a vascular clamp, for a simplified handing. With the use of such a surgical instrument, in particular particularly importance is given to the operating (handling) of the instrument, in order to avoid possible injuries to organs, vessels and suchlike and/or traumatic consequences resulting therefrom. An important criterion in operations is to reduce the number of instruments which are necessarily required and/or to reduce the overall size of the instruments. A reduction of individual surgical instruments in the operation is generally very difficult, so that attention is directed to reducing the overall size of instruments and the ability of the instruments to be dismantled. The ability to be dismantled is understood here to mean the dismantling of an instrument into different components, wherein the individual components are compatible with one another and therefore enable a reduction of surgical instruments. In order to achieve an ability of individual components to be combined, means having an identical effect are to be used in the coupling elements.

Accordingly, it is an object of the present invention to produce a surgical vascular clamp which is equipped with a coupling arrangement, an adjusting arrangement in combination with an arresting arrangement, according to EP 2 335 609 B1, in order to achieve a compatibility with an existing supply- and removal device, consisting of an operating arrangement and an actuating tool. The surgical instrument of EP 2 335 609 B1 which is able to be dismantled into three components forms the basis of the further development. The supply- and removal device or respectively the two components, the operating arrangement and the actuating tool with instrument grip, are also to be able to be used for other, differently constructed vascular clamps and therefore are to be usable again in a multiple manner, in order to reduce the disorder of instruments at the operation site. This means that the supply- and removal device is to be used for various embodiments of surgical instruments, in so far as these are equipped with corresponding coupling means.

It is a further object of the invention to provide the differently constructed vascular clamps in the embodiment with coupling means according to EP 2 335 609 B1, which are compatible with the supply- and removal device and which substantially facilitate the handling of the surgical instrument, in particular the vascular clamp of the invention, and therefore configure it more safely, and to avoid coupling means, e.g. bayonet closures, as known from DE 602 24 460 T2 and DE 197 19 090 A1.

The vascular clamp of the invention therefore has a coupling arrangement, an adjusting arrangement and an arresting arrangement, according to EP 2 335 609 B1. The retaining jaws of the coupling arrangement on the vascular clamp correspond here with the gripping elements of the gripping arrangement on the operating arrangement or respectively on the carrier instrument. Furthermore, the adjusting element of the adjusting arrangement, arranged on the vascular clamp, corresponds with the tool blade, arranged on the actuating tool, and the arresting arrangement corresponds with the adjusting arrangement. The vascular clamp of the invention must be constructed such that the supply- and removal device can grip, clamp, guide and accordingly release the vascular clamp again, wherein the actuating tool can adjust the movable branches of the operating means continuously via the adjusting arrangement, in connection with the tension- and pressure element. The arresting of the adjustable branches takes place via an arresting arrangement. For the advantageous embodiment of a complete surgical instrument, reference is to be made to the extensive descriptions in EP 2 335 609 B1. To solve the problem, it is proposed that the stationary body element of the vascular clamp is therefore equipped with a coupling arrangement, which corresponds with a supply- and removal device of EP 2 335 609 B1.

A further object consists in constructing a vascular clamp, able to be operated with a supply- and removal device, with two branches opening and closing in a parallel manner. The solution to this problem is led to by the movable branches being connected via a front and rear parallelogram-like articulated connection with the body element, wherein the articulated connections form a lever gear with the body element.

The surgical instrument resulting from the problems to be solved and in the development, in particular in the embodiment of an operating means, guided in a parallel manner, consisting of two branches on a vascular clamp, was adapted according to the invention to the instruments which are able to be dismantled and completed in three parts, in order to keep the opening in the thorax free from the surgical instrument required during the operation. The components of the surgical instrument, which are able to be dismantled and completed in three parts, concern an operating arrangement, an actuating tool and, as described below, an inventive vascular clamp. This means that the solution to the problem consists in producing a vascular clamp with branches able to be adjusted continuously in a parallel manner, which is adapted to the handling of a surgical instrument able to be dismantled and completed, and corresponds with the individual instrument parts of another surgical instrument. The solution is to be found again in the inventive features which are specified in the claims. The advantageous embodiments of the inventive surgical instrument can be seen from the description below.

The solution to this problem consists in developing a continuously gripping and clamping vascular clamp with at least one branch, opening and closing in a parallel manner, according to FIG. 2. The vascular clamp is basically a technical system which is joined together from a plurality of different technical components, or respectively of individual elements. The individual components or respectively elements of the vascular clamp comprise a body element, a tension- and pressure element, at the distal end an operating means, which consist of two branches. The two branches are able to be actuated relative to one another from a completely open position into a completely closed position, wherein the movable branches are arranged on a front and rear parallelogram-like articulated connection. The articulated connections have a front and a rear articulation axis, which are connected with the body element. At the proximal end of the vascular clamp there is a coupling arrangement, consisting of two retaining jaws. The retaining jaws serve to receive a detachable supply- and removal device, which is able to be operated by the surgeon. Furthermore, the vascular clamp has an adjusting arrangement in combination with an arresting arrangement, wherein the adjusting arrangement serves to receive a detachable actuating tool. The actuating tool in connection the adjusting arrangement undertakes via the tension- and pressure element a continuous adjusting of the two branches, whereby an opening and closing of the operating means takes place.

The core of the invention in the case of the vascular clamp comprises a lever gear, consisting of a lever mechanism. The operating principle of the lever gear is basically a technological process, in which the interaction of the physical and geometric processes takes place in the interplay with the above-mentioned components or respectively elements, and which is described below. The interacting components and elements concern a stationary lever, which is constructed as a body element. Arranged onto the body element are a coupling arrangement, an adjusting arrangement, to which a tension- and pressure element adjoins, and an arresting arrangement. This body element with the elements arranged thereon forms the basis of the vascular clamp and the further inventive activity. The inventive development consists in providing a body element with parallelogram-like articulated connections and forming a corresponding adjustment for the parallelogram-like articulated connections, in order to obtain an operating means gripping in a parallel manner and adjustable continuously. The problems therefore consist in finding an arrangement of the parallelogram-like articulated connections on the body element, previously equipped with various elements, and in providing a corresponding adjustment of these articulated connections. These problems are solved in that the body element of the vascular clamp is a component of the inventive lever gear.

According to the invention, these problems are solved by the characterizing features of Claim 1. Advantageous embodiments and further developments of the invention will emerge from the following subclaims and the description.

The vascular clamp comprises a lever gear which consists of a stationary lever, which is constructed as a body element. The body element, in turn, has two axially displaceable elements, which are arranged along the centre line of the body element, and above and below the body element and spaced in a parallel manner through this. These two spaced elements form a tension- and pressure element and a push-pull rod, which are connected securely with one another via a connecting element. When the tension- and pressure element is displaced via the adjusting arrangement, arranged on the body element, the push-pull rod moves simultaneously, owing to the fixed connection to the tension- and pressure element, automatically by the same amount. The displacement of the tension- and pressure element can take place both forwards and backwards, wherein the push-pull rod likewise follows this displacement. Furthermore, the lever gear comprises six rotationally movable levers, which are formed from two branches I, II spaced in a parallel manner, two pivot arms I, II and two toggle levers I, II. The branches I, II are spaced longitudinally and parallel to the centre line of the body element and are connected via the pivot arms I, II and the toggle levers I, II with the body element in a rotationally movable manner at the free end of the body element. The connection of the pivot arms I, II and the toggle levers I, II on the body element runs perpendicularly to the coupling arrangement arranged at the proximal end. One of the two pivot arms I consists of a pair of pivot arms I, which are connected to the body element with the same articulation axis V as the opposite pivot arm II. Respectively a branch I, II, a pivot arm I, II and a toggle lever I, II form together with the body element a parallelogram-like articulated connection, so that the lever gear consists of two parallelogram-like articulated connections.

For fastening the pivot arms I, II and the toggle levers I, II on the body element, the latter has three joint axes I, I', V and three grooves I, II, III. In total, however, four grooves I, II, III, IV are formed in the body element. A first groove I is arranged at the free end of the body element and forms a fork head. This fork head serves to receive a pivot arm II, which produces the connection between the body element and a branch II. The first front articulation axis V, which also receives the pair of pivot arms I which produces the connection between the body element and the other branch I, runs perpendicularly to the fork head and the first groove I. The pair of pivot arms I, however is fastened in a rotationally movable manner outside, or respectively externally on the fork head on the first front articulation axis V. The front articulated connection therefore has a shared articulation axis V on the body element. Two further grooves II, III, formed in the body element, follow at a certain distance from the first articulation axis V, following on from the groove I arranged at the free end, or respectively fork head. One of the two grooves II, III above II and the other grooves below III of the body element is let into the latter. The two grooves II, III (second and third groove), opposite one another and spaced in a parallel manner, are arranged perpendicularly to the centre line of the body element and have respectively an articulation axis I, I' (second and third articulation axis). These two joint axes I, I' serve for the rotationally movable fastening for respectively a short lever arm of a toggle lever I, II. These toggle levers I, II form the connection between the body element and a branch I, II. The arrangement of the fourth groove IV in turn, viewed from the free end of the body element and the second and third articulation axes I, I' lying between, is spaced apart therefrom. The fourth groove IV likewise runs, like the two grooves II, III for the articulation axes I, I' of the toggle levers I, II, in perpendicular direction to the centre line and perpendicularly to the first three articulation axes I, I', V arranged in the body element. The fourth groove IV is arranged running continuously through the body element, i.e. the groove IV connects the upper side and the underside of the body element with a continuous slot. Furthermore, the slot has a slot length which corresponds at least to the path length s of the linear displacement of the tension- and pressure element, wherein the slot serves for the guidance of a connecting element. The connecting element secures the fixed connection between the tension- and pressure element and the push-pull rod. An adjustment of the tension- and pressure element necessarily brings about an adjusting of the push-pull rod. This is also necessary so that the two branches I, II of the operating means can move simultaneously towards one another or away from one another.

The tension- and pressure element is therefore arranged for the adjustment of the one branch I, II via a rotationally movable articulation axis II, on the short lever arm of the one toggle lever I, which produces the connection to the first branch I. The push-pull rod, securely connected with the tension- and pressure element, on the other hand, is arranged via an articulation axis II' on the short lever arm of the second toggle lever II, which produces the connection to the second branch II. A toggle lever I, II is formed respectively from a short and a long lever arm, wherein respectively on the long lever arm a joint head is formed. A joint head at the free end of a long lever arm is received by a fork head arranged at the free end of a branch I, II. A joint head and a fork head form a knee joint. The connection of the knee joint takes place via an articulation axis III, III'. Thereby, a continuous connection is provided from the actuating tool to the adjustment of the branches I, II of an operating means. The parallel guidance of the two branches I, II is now still to be ensured. For this, a pivot arm II and a pair of pivot arms I are arranged on the body element, which produce the connection to the branches I, II. By the arrangement of the pivot arms I, II, the branches I, II are positively guided, whereas, however, the drive for the adjustment of the branches I, II takes place via the two toggle levers I, II.

The interacting components and elements are a stationary lever, which is constructed as a body element, and at least one movable lever, preferably several movable levers, consisting of a tension- and pressure element, at least one toggle lever I, II, at least one pivot arm I, II and at least one movable branch I, II. Only the correct geometric design and the correct advantageous interplay of these components make possible at least one branch I, II, opening and closing in a parallel manner, on the vascular clamp. In an advantageous manner, the body element in this lever gear forms the stationary lever and the tension- and pressure element arranged thereon forms the first displaceable lever. This first displaceable lever is displaceable linearly via an external drive according to the screw/nut principle (actuating tool with instrument grip). The displacement of the tension- and pressure element acts in turn on a first toggle lever I, pivotable about an angle, which on the one hand is fastened on the stationary lever, formed from the body element, and on the other hand carries a lever which is articulated adjustably on the knee joint, which lever consists of a movable branch I. The movable branch I acts in turn on two further pivot arms I fastened thereon, which are constructed as a pair and which are likewise fastened on the stationary lever, the body element, in an advantageous manner. As the tension- and pressure element is securely connected with the push-pull rod, the push-pull rod, in an analogous manner to the tension- and pressure element, acts on a second toggle lever II, pivotable about an angle, which on the one hand is also fastened to the body element and on the other hand carries a branch II, movably arranged on the knee joint. This movable branch II is also connected with the body element via a pivot arm II.

For the functioning of the lever gear, the latter therefore has six movable levers. Owing to the symmetrical characteristics of the lever gear, respectively three levers are arranged on one side of the centre line of the body element and three levers are arranged mirror-symmetrically on the other side of the centre line of the body element. Three of the levers, arranged in a rotationally movable manner on one side (above) the centre line are connected with one another with five articulation axes I, II, III, IV, V. Of these five articulation axes I, II, III, IV, V, three articulation axes I, I', V are arranged in the stationary body element and serve as a rotation point for the two pivot arms I, II fastened thereon and the two toggle levers I, II. The other two articulation axes III, IV or respectively III', IV' are movably arranged and can be displaced about an angle within a particular angle range. The same applies for the three levers arranged on the other side of the centre line, i.e. the symmetrically opposite levers on the centre line are congruent.

This means that the stationary body element is connected with a first pivot arm I, arranged thereon, and a first toggle lever I, arranged thereon, via five articulation axes I, II, III, IV, V with a first branch I and with a second pivot arm II, arranged thereon, and with a second toggle lever II likewise via five articulation axes I, II, III, IV, V with the second branch II, wherein articulation joint axes I, I', V, stationary in the body element, serve as rotation point for two pivot arms I, II and as rotation point for two toggle levers I, II and three articulation axes II, II', III, III, IV, IV' arranged movably on a circular arc, are displaceable about an angle α, β, γ, α', γ'.

This lever gear advantageously converts a linear movement or respectively a displacement of the tension- and pressure element and of the push-pull rod into a resulting displacement of the two movable branches I, II. The linear movement of the tension- and pressure element takes place basically through a screw-nut drive. The drive of the screw/nut drive is produced by a rotary movement or respectively by a particular number of revolutions of the instrument grip on the actuating tool, wherein the revolutions of the actuating tool are transferred to the adjusting arrangement. The rotary movements of the actuating tool can take place both forwards and backwards or respectively to the left or to the right. A right rotation on the actuating tool allows the tension- and pressure element and the push-pull rod to withdraw by a particular path length s. On withdrawing of the tension- and pressure element and of the push-pull rod, the branches I, II of the operating means open. A left rotation on the actuating tool produces a linear displacement of the tension- and pressure element, and of the push-pull rod, about a particular path length s in a forward direction. On the forward pushing of the tension- and pressure element and of the push-pull rod, the branches I, II of the operating means close. By a rotary movement on the actuating tool, a resulting displacement of the branches I, II in two directions, a closing direction or an opening direction, is brought about. The relationship of the rotary movements on the actuating tool to the linear displacement of the tension- and pressure element and therefore also to the push-pull rod is approximately 1:0.4. This is a reduction ratio in the screw/nut drive. This reduction is a prerequisite for a good adjusting of the power transmission to the vascular clamp. A plurality of revolutions on the actuating tool produces a small linear displacement of the tension- and pressure element and of the push-pull rod. The lever gear according to the invention converts this relatively small linear displacement (path length s) of the tension- and pressure element, owing to a transmission ratio of the lever gear of approximately 1:12, again into a greater opening of the operating means (path length X) or respectively displacement of the branches I, II. For this lever transmission, an inventive design of the toggle levers I, II is necessary. A toggle lever I, II therefore consists of a bent joint lever. Such a bent joint lever is formed from a short and a long lever arm. The long lever arm of a toggle lever I, II has at the free end a joint head with an eye, whilst on the short lever arm a spring is arranged having two openings for receiving two articulation axes I, II. Two pivot arms I, II and two toggle levers I, II rotationally movably via the articulation axes III, III', IV, IV' are carriers of the displaceable branches I, II. The displaceable branches I, II have at one end a fork head with an opening arranged perpendicularly thereto, for receiving an articulation axis III, III' for a knee joint, and, spaced with respect thereto, an opening for receiving an articulation axis IV, IV' for a pivot arm I, II.

A linear displacement of the tension- and pressure element and of the push-pull rod on a path length s results in an angular displacement about the three articulation axes I, I', II, II', III, III' of the toggle levers I, II in the angle range α, β and an angular displacement of the two articulation axes IV, IV' of the pivot arms I, II with the movable branches I, II in the angle range γ.

By the example of an opened operating means, it is to be described which path the two branches I, II, spaced in a parallel manner and displaceable, cover from the opened position up to the closed position. The two displaceable branches I, II form two straight lines, which point in the same direction, wherein the straight lines are not adjacent to one another but are spaced in a parallel manner over one another, i.e. each branch I, II lies in its own plane, wherein the planes are arrange parallel to one another. The upper displaceable branch I is situated in the upper plane and the lower displaceable branch II is situated in the lower plane. The branches I, II are opposite one another, spaced approximately parallel, in the opened position of the operating means. If the operating means, as previously described, is now closed, the branches I, II move, owing to the lever action of the pivot arms I, II and toggle levers I, II. The branches I, II move respectively in their plane forward and at the same time a movement of the branches I, II takes place and therefore of the planes, towards one another. Therefore, the closing movement of the operating means is understood as a parallel displacement of the movable branches I, II in a plane, e.g. in horizontal X direction, and a displacement of the planes towards one another. This is understood to mean a parallel displacement of two planes towards one another, e.g. in perpendicular Z direction. A horizontal displacement of the movable branches I, II in Y direction does not take place. As the two movements of the displaceable branches I, II in X and Z direction take place simultaneously, a resulting direction is produced for the displacement of the movable branches I, II which is composed of the portions of the X and Z direction. This means that the upper plane, formed from the area ($X_o$ times $Y_o$) approaches the lower plane, spaced in a parallel manner, formed from the area ($X_u$ times $Y_u$) via a perpendicular plane lying therebetween, formed from the area ($X_n$ times $Z_n$). The displacement of the upper plane in the direction (X, Z) of the lower plane takes place on the resulting direction $\Delta_{res}=\Delta X+\Delta Z$, which lies in the spanned plane ($X_n$ times $Z_n$). The movable branches I, II move towards one another in this resulting direction $\Delta_{res}=\Delta X+\Delta Z$, owing to the movement of the toggle levers I, II, or move away therefrom reciprocally.

In opened position of the operating means, the extended centre line of the body element forms basically two virtual trapeziums with the movable branches I, II articulated via the pivot arms I, II, which branches are both spaced in a parallel manner. As the two trapeziums are mirror-symmetrical, only one trapezium has to be described as an example. Presented differently, the centre line of the body element forms with its functional regions I and II (more concerning the functional regions below), the base line a of a virtual trapezium. The base line a with the corner points A and B has in the corner point B an articulation axis V, which forms the lower rotation point of the pivot arms I, II. The pivot arms I, II themselves form the right side line c or respectively c' of the trapezium, which is delimited by the corner point B and C. The side line c has in the corner point C a articulation axis IV with an upper rotation point for the pivot arms I, II. The top line b or respectively b', which is formed by the movable branch I, II, is spaced in a parallel manner to the base line a. The top line b, b', with corner points C and D, has in the corner point C the articulation axis IV, which forms the upper rotation point of the pivot arms I, II, whilst the corner point D, D' is situated at the free end of the movable branch I, II. The imaginary left side line d (opening of the operating means) of the trapezium is situated between the corner points D and A. The corner point D does not stand perpendicularly over the corner point A, and likewise the corner point C not over the corner point B, wherein the corner points B and C form the articulated connection between the branches I, II of the operating means. On closing of the operating means, the movement sequence, in relation to the observation of a trapezium, is as follows: On pivoting of the toggle lever I, II in forwards direction, angles α, α' and angles β, β' become smaller, this moves the movable branch I, II about the rotation point in the articulation axis III, III', whereby a displacement of the imaginary top line b takes place. Owing to the fact that the movable branch I, II has a further rotation point C, C' in the articulation axis IV, IV', which is spaced apart by a particular extent from the rotation point in articulation axis III, III', the movable branch I, II is positively guided. The movably guided branch I, II, fastened by the two articulation axes III, III' and IV, IV' on the toggle lever I, II and the pivot arms I, II, carries out a consistent movement, owing to the two-point guide. The branch I, II follows this movement, which is provided by the pivot arms I, II and the toggle lever I, II. As the pivot arm I, II is fastened in a rotationally movable manner on the articulation axis V and the toggle lever I, II on the articulation axis I, I' of the stationary lever or respectively of the body element, the movable branch I, II can only be guided on a circular arc. This movement guides the movable branch I in a parallel manner towards the opposite movable branch II or in a parallel manner away therefrom. The size of the circular arc is determined by the provided length of the pivot arms I, II and of the toggle levers I, II. In relation to the figurative illustration with the trapezium, this means that the displaceable branches I, II on closing of the operating means always draw nearer or distance themselves in a parallel manner with respect to one another, depending on whether the operating means is opened or closed. This means that the base line a lies in a plane and the top line b, b' lies in a plane, wherein the three planes are spaced in a parallel manner with respect to each other. The centre line of the body element lying in the base plane (base line a) of the body element and the two displaceable branches I, II lying in the top plane (top line b, b') can move closer to or away from one another in a parallel manner. Both branches I, II have, lying in their planes, the same direction (X direction). In longitudinal direction (X direction), viewed towards the free end of the two branches I, II, in opened position of the operating means and with the greatest possible distance of the displaceable branches I, II to the centre line of the body element, i.e. the greatest possible distance between the two planes, the free ends of the two branches I, II or respectively the two corner points A and D are furthest apart from one another and do not stand perpendicularly over one another, although the free ends of the two branches I, II and therefore the corner points D, D' thereof always stand perpendicularly to one another. Only on closing of the operating means or respectively on displacing of the movable branches I, II and therefore of the top planes (top line b, b') towards the base plane (base line a) does the corner point D. D' draw nearer to the corner point A, as previously described, via a circular path. This means that on closing of the operating means, the movable branches I, II move on the one hand in their top plane (top line b, b') and on the other hand the top planes (top line b, b') draw nearer to the base plane (base line a) in a parallel manner. When the planes b, b' lie against the plane a, the branches I, II, and therefore the operating means, are closed. The same applies in the reverse sense, when the operating means is opened and the displaceable branches I, II move away from one another. The top plane (top line b, b') then moves in a parallel manner to the base plane (base line a) on a radius which is guided on a circular arc up to the maximum end position. Basically, in the invention there is a displacement of two movable branches I, II in a plane and a displacement of these planes towards a central plane, or away therefrom. Owing to this simultaneous displacement of the branches I, II in two different directions, a resulting displacement of the movable branches I, II occurs on a circular path sector. This alternating movement of the displaceable branches I, II for opening and closing a vascular clamp is produced by the lever gear according to the invention. Owing to the inventive arrangement and design of the lever mechanism for the opening and closing movement of the displaceable branch in the operating means, the movement takes place simultaneously in horizontal and vertical direction.

The transition from a closed position of the operating means to an open position concerns the reverse movement direction. The movable branches I, II are guided parallel to the centre line of the body element on the resulting direction formed from the X and Z direction, wherein simultaneously the two free ends of the movable branches I, II move away from the corner point A of the trapezium. This displacement of the movable branches I, II away from the centre line of the body element does not take place perpendicularly, but rather, as previously indicated, on a resulting circular arc.

The linear movement of the tension- and pressure element is alternating in every position, and therefore also the movement of the push-pull rod, whereby an opening and closing of the operating means of the vascular clamp can take place in every position between maximum opening and closed branches I, II. For this, the toggle levers I, II, similar to a crank drive, are displaced by the tension- and pressure element and by the push-pull rod about an angle ϑ, ϑ' in a particular angle range α, α'. Here, the linear path s of the tension- and pressure element and of the push-pull rod is changed into a circular path b, wherein the length b corresponds to the arc length on a circular arc. The length b corresponds approximately with the length s and therefore determines the possible adjustable angle range α, α' of the toggle levers I, II, wherein b is also proportional to the angle α, α' and to the radius r. The radius r is determined by the distance of the two articulation axes I, II and I', II', which are arranged on the toggle levers I, II. The articulation axis I, I' forms the rotation point of the toggle levers I, II and enables a pivotable movement therefore about this rotation point, wherein the articulation axis I, I' is fixedly arranged in the body element. The articulation axis II, II' forms with respect to the articulation axis I, I' on the toggle levers I, II a spaced point of application for the tension- and pressure element and for the push-pull rod. The tension- and pressure element is therefore connected with the toggle lever I at the articulation axis II and can move the toggle lever I forwards and backwards by means of the articulation axis II. As the push-pull rod is connected on the articulation axis II' with the toggle lever II, this can move the toggle lever II forwards and backwards by means of the articulation axis II'. The joint axes II, II' are arranged movably or respective displaceably owing to the displacement along a circular arc. The extent of the displacement of the toggle levers I, II is determined by the distance r of the two articulation axes I, II and I, II' and the linear path s of the tension- and pressure element. This means that from the two parameters r and s, a particular angle α, α' is produced, which determines the pivoting range of the toggle lever I, II and therefore the pivoting range of the articulation axis II, II' and III, III'. The pivoting range therefore results from the length of the linear path s of the tension- and pressure element, which amounts to approximately 5 mm and from the distance r of the two articulation axes I, II and II, II', which is likewise approximately 5 mm. The pivoting range resulting therefrom for the toggle levers I, II has an angle range α, α' for adjusting the toggle levers I, II and therefore for adjusting the branches I, II arranged on the toggle levers I, II, from approximately 0 degrees up to 90 degrees, preferably from 10 degrees up to approximately 80 degrees. Furthermore, the toggle levers I, II have a third articulation axis III, III', about which a branch I, II is again movably arranged. On the basis of a predetermined length L of a toggle lever I, II and the predetermined length of the pivot arms I, II, the operating means of the vascular clamp can take up a variable opening between the movable branches I, II in the range of 0 mm up to approximately 60 mm. Each change to the extent of opening between 0 mm and 60 mm between the two branches I, II can take place continuously via the adjustable tension- and pressure element. An additional change to the extent of opening can be achieved via the structural change of a parameter, the axis distance r between the articulation axis I, II and the articulation axis I', II', whereby the path of the radian b of the articulation axis II, II' can alter owing to a greater radius r on the circumference of the circular arc. A further structural change to the extent of opening can also result through a change to the linear path length s of the tension- and pressure element, which enables a change to the arc length b. Furthermore, the lengths of the lever arms (pivot arms I, II and toggle levers I, II) can be structurally changed. The changing of all three parameters is also possible and leads to a change of the extent of the opening of the operating means and therefore of the vascular clamp. Generally, an opening of the vascular clamp in the range of 0 mm up to 40 mm is sufficient for the surgeon for the gripping of tissue and similar. If required, vascular clamps can be used with different opening extents on the operating means which, owing to the compatibility with the existing instruments, only have to be exchanged.

The body element as stationary lever and part of the lever gear of a vascular clamp forms here the basis of the instrument and is the carrier of all components or respectively all elements which are connected fixedly or movably with the body element. The movably arranged branches I, II, which are in relation or respectively are connected indirectly with the body element via the lever mechanism form an exception.

The body element is advantageously produced from a one-piece, solid, low-corrosion metal, preferably high-grade steel, titanium or tantalum. It has two free ends, which are situated on an imaginary straight centre line, and consists of two branches, displaceable in a parallel manner on two circular arcs, which are connected via a front part of pivot arms with the body element and with a rear pair of toggle levers, which are connected with the tension- and pressure element, the push-pull rod and the body element. Furthermore, the one-piece body element is constructed so as to be relatively elongated and narrow. This means, in relation to the size of the cross-section, dimensions in the range of approximately 5 mm×approximately 9 mm, wherein 9 mm form the height and the 5 mm form the width of the body element, without taking into consideration the adjusting arrangement and coupling arrangement. In relation to the elongated dimensions, the size results in a range of approximately 50 mm to 60 mm, preferably in the range of around 55 mm. The vascular clamp basically has three functional regions I, II, III. The three functional regions I, II, III concern the operating means in the functional region I, the lever gear in the functional region II and a carrier part in the functional region III. The first functional region I, which concerns the operating means of the vascular clamp, has two branches I, II which are displaceable in a parallel manner. The two branches I, II have a shape which runs in a straight line and tapering from the free end of the body element towards the free distal end of the operating means. Furthermore, the displaceable branches I, II arranged in the functional region I are movably connected with the pivot arms I, II. On the face side, the freely standing distal end of the operating means is rounded, in order to prevent injuries e.g. to the tissue. Both branches I, II are provided with an advantageous toothing known from the prior art and/or with an exchangeable pad, wherein the length of the branch I, II is approximately ¼ to ½, preferably approximately ⅓ of the total length of the vascular clamp. In another embodiment, the length of the toothing can be half the total length of the vascular clamp. The width of the branch I, II, which tapers towards the free end, is narrower on its length than the width of the centre part and the width of the carrier part and therefore the narrowest region of the body element.

The second functional region II consists of the centre part. The centre part presents for the most part the lever mechanism according to the invention. The lever mechanism in the centre part of the vascular clamp consists of two articulated pivot arms I, II and two articulated toggle levers I, II, wherein the pivot arms I, II and the toggle levers I, II are articulated on the one hand on the body element and on the other hand on the branches I, II. A pivot arm I, II and a toggle lever I, II are spaced in an approximately parallel manner and therefore point in the same direction. Each of these pivot arms I, II and toggle levers I, II is arranged movably on the body element and extends in the direction of the branches I, II arranged parallel to the body element. The centre part of the vascular clamp has at the corresponding site on the body element an articulation axis V, on which the two pivot arms I, II are arranged in a rotationally movable manner. This movable arrangement or respectively articulated connection enables the pivot arms I, II to carry out a rotary movement about the rotation point of the articulation axis V. The rotary movement of the pivot arms I, II is limited, however, to a pivoting movement between approximately 0 degrees and 90 degrees. Owing to the alternating linear movement of the tension- and pressure element, a pivoting movement of the pivot arms I, II in both directions, forwards and backwards, i.e. clockwise and anticlockwise, is possible. Only one degree of freedom exists for the movement direction, further degrees of freedom do not exist. Owing to the pivoting movement of the pivot arms I, II, a parallel opening and closing of the operating means through the movably arranged branch I, II is possible. The pivoting movement of the pivot arms I, II is positively guided and is enforced through the displacement of the toggle levers I, II. As a pair of pivot arms I are articulated at the free end of the body element, these can receive between them, on closing of the operating means or respectively on closing of the movable branches I, II, the pivot arm II, which is arranged centrally at the free end of the body element. The width of the centre part is narrower on its length than the width of the carrier part, but is also wider than the width of the movable branches I, II, wherein the length of the centre part is approximately ⅛ to ⅜, preferably approximately ⅓ of the total length of the vascular clamp, and can have an approximately square cross-section, because the height and width of the cross-section section of the centre part is approximately identical.

The other free end of the vascular clamp, towards the proximal end, which lies in the functional region III, has an approximately rectangular cross-section. The width of the cross-section is smaller than the height of the cross-section. Furthermore, the cross-section at the proximal end of the branch is approximately twice as great as the cross-section at the distal end. The length of the rectangular cross-section is approximately ¼ to ½, preferably approximately ⅓ of the total length of the vascular clamp, which represents the functional region III and is constructed as a carrier part. Owing to the rectangular cross-section, four sides are present with respectively a flat surface, two side faces, one face on the underside and one face on the upper side, which are all required and used for various functions. The carrier part has a retaining jaw respectively on the two side faces which are spaced in a parallel manner with respect to each other, towards the proximal end of the body element. The two retaining jaws, spaced in a parallel manner and lying opposite one another, are connected in one piece with the body element and form the coupling means of the coupling arrangement. The coupling arrangement serves the gripping arrangement, arranged on the operating arrangement (carrier instrument) for grasping and releasing the vascular clamp. On grasping of the vascular clamp, simultaneously the actuating tool with instrument grip is centred to the adjusting element and brought into engagement. The adjusting element is part of the adjusting arrangement, which is arranged on the upper side of the carrier part in the functional region III, wherein the mount, arranged on the upper side, for the adjusting arrangement is connected in one piece with the body element.

Furthermore, an arresting arrangement is situated in the functional region III at the proximal face end. The arresting arrangement is formed from a leaf spring and an arresting pin, guided in a bore, which arresting pin engages into a detent profile arranged in an adjusting element. The detent profile in the adjusting element basically consists of blind bores arranged in a row adjacent to one another, or respectively only of the indicated bores having a small depth. The indicated bores are produced by the centring point of a drill. The centring point of a drill basically produces a cone-shaped depression. These depressions are arranged on the circumference of the adjusting element. An arresting pin engages into respectively one of these depressions. The leaf spring of the arresting arrangement is fastened to the underside of the body element in the region of the carrier part and exerts a particular force onto the arresting pin, so that the latter always engages into a depression in the adjusting element. On the face side, the freely standing, proximal end of the carrier part, in which the bore for the arresting pin is situated, is rounded, in order to prevent injuries e.g. to the tissue.

The adjusting arrangement with the tension- and pressure element is situated on the upper side of the body element in the functional region III, connecting on to the carrier part. The tension- and pressure element is connected on the one hand via a connecting element with the adjusting element of the adjusting arrangement and on the other hand, on the side lying opposite the connecting element, with a toggle lever I of the lever mechanism. The toggle lever I is a bent lever, a so-called angle lever. The angle lever is formed from two lever arms, wherein the length of the lever arms is different. The ratio of the length of the lever arms to one another is approximately 1:4 between the short and long arm. The angle between the shorter and longer lever arm of the toggle lever I, II is approximately 100 degrees to 150 degrees, preferably 135 degrees. Furthermore, the toggle lever I, II, consisting of two lever arms, is constructed as a joint lever. Two openings, preferably constructed as bores, are arranged on the shorter lever arm, which serve to receive an axis respectively. Furthermore, the shorter lever arm is constructed narrower than the longer lever arm of the toggle lever I, II. The narrower short lever arm has the form of a spring, which engages on the one hand into a groove which is arranged in the functional region III of the carrier part, and on the other hand into a groove of the tension- and pressure element which is formed in a fork-like manner. The other end of the toggle lever I, II has a joint head with an eye. The joint head forms with the end of the movable branch I, II, formed in a fork-like manner, an articulated connection, or respectively a hinge, which, as a connecting joint, connects two parts (branch and toggle lever) movably with one another. The information previously given with regard to the tension- and pressure element apply in an analogous manner to the push-pull rod arranged on the body element. The pull-push rod is securely connected with the tension- and pressure element via a connecting element. Furthermore, the push-pull rod is likewise connected with a toggle lever II of the lever gear. The toggle lever II has the same dimensions and characteristics as the toggle lever I arranged on the tension- and pressure element, and therefore does not need to be described once again. This toggle lever II arranged on the push-pull rod also has a joint head, which is connected with a branch II.

The joint receives both the load of the movable part and also the force of the movement, wherein the joint has only one degree of freedom. The input parameter for the force is determined by the actuating tool with instrument grip and acts via the screw/nut gear, the linear adjustment of the tension- and pressure element and the lever mechanism on the branches I, II which are adjustable in a parallel manner. Owing to the reduction by the screw/nut gear, the force generated by the instrument grip is firstly intensified and subsequently reduced somewhat again owing to the transmission of the lever mechanism, wherein the lever mechanism determines the input parameter of the force along the path and therefore the changeable ratio. A fork head and a joint head are articulatedly connected with one another via the articulation axis III, III', wherein only the toggle levers I, II perform a rotary movement about the rotation point of the axis III, III'. This means that only the joint heads of the toggle levers I, II can undertake a rotary movement in the fork heads of the branches I, II. The reason for this is that the movable branches I, II are connected with the stationary lever of the body element via the pivot arms I, II. Owing to this connection, the movable branches I, II are positively guided. The positive guidance always ensures the parallel position of the displaceable branches I, II. Owing to the parallel position of the movable branches I, II, irrespective of whether the operating means are completely open or completely closed or guided towards one another or away from one another, the fork heads remain in a particular position and only the joint heads of the knee joints perform a rotary movement. The rotary movement of the toggle levers I, II is, however, established to a particular angle range. This angle range between the movable branches I, II and the knee joints amounts to approximately between 90 degrees and 180 degrees. The joint heads on the long lever arms of the toggle levers I, II can perform in the fork heads of the branches I, II a pivoting in the above-mentioned angle range of up to 90 degrees. With the pivoting movement of the toggle levers I, II, the pivot arms I, II of the branches I, II and the toggle levers I, II are pivoted towards one another or away from one another in the above-mentioned angle range, through approximately 90 degrees.

The inventive vascular clamp, in particular used as an aorta clamp in laparoscopic operations on the infrarenal aorta, ensures by means of an operating arrangement and an actuating tool, a secure clamping-off also of sclerotic vessels. A rotary closure with a fine thread permits a regulated closing and opening of the branches I, II, displaceable in a parallel manner, of a vascular clamp. And through the use of exchangeable pad inserts on the branches I, II of the vascular clamp according to the invention, an atraumatic clamping of vessels is improved. The setting of the pressure force which can be set via the lever gear, owing to the transmissions, in a regulated manner onto a tissue or vessel, also makes it possible to regulate the through-flow of a fluid in the case of a vessel. Owing to the possibility for regulating, the operator can proceed in a manner which is as protective of soft tissue as possible during the operation. Such a possibility assists an atraumatic manner of proceeding during the operation. This manner of proceeding is made possible by the inventive vascular clamp, wherein the latter offers the further advantage which lies in the reliability of the vascular clamp to mechanically close a vessel autraumatically in a reliable manner. The pressure force for the displaceable branch I, II on the operating part of the vascular clamp is produced by rotations of the instrument grip on the actuating tool. Rotations of the instrument grip bring about a displacement of the tension- and pressure element which is connected via a fine thread. The tension- and pressure element then acts on the branch I, II via the levers of the lever gear. Furthermore, the inventive vascular clamp is formed only from a small number of clearly arranged components, whereby also the cleaning and disinfecting of the vascular clamp is substantially facilitated.

The present invention relates to such a medical instrument which can be used in particular in cardiology as a minimally invasive surgical instrument, for example in the embodiment of a continuously gripping and clamping vascular clamp, which is suitable for the occluding of tubular organic human or animal body parts, such as blood vessels, preferably arteries and suchlike, for minimally invasive surgical interventions. The vascular clamp comprises a body element, a tension- and pressure element and, at the distal end, an operating means with two branches which, relative to one another, are able to be actuated from a completely open position into a completely closed position, wherein the movable branches are arranged on a front and rear parallelogram-like articulated connection, wherein the articulated connections have a front and rear articulation axis which are connected with the body element. At the proximal end, a coupling arrangement, consisting of two retaining jaws, is arranged. The coupling arrangement serves for the receiving of a detachable supply- and removal device, which comprises a gripping arrangement, an operating arrangement and an actuating tool. The supply- and removal device enables the introducing and removing of the vascular clamp through a body opening and is operable by a surgeon.

Furthermore, at the proximal end of the vascular clamp there is situated an adjusting arrangement in combination with an arresting arrangement, wherein the adjusting arrangement serves for receiving a detachable actuating tool with a rotary grip (handling part with instrument grip). The actuating tool is connected with a tension- and pressure element via an adjusting arrangement and enables the opening and closing of an operating means. The operating means consists of branches, movable parallel to one another, which can be adjusted continuously. Such a medical instrument concerns a minimally invasive surgical instrument able to be dismantled into three components, which enables a free access for other instruments through the body opening and therefore reduces the amount of instruments in the opening. The surgical instrument, able to be dismantled into three components, comprises a vascular clamp (operating instrument) and a supply- and removal device (carrier instrument or respectively shaft part), which consists of an operating arrangement and an actuating tool (handling part together with instrument grip).

BRIEF DESCRIPTION OF THE DRAWINGS

Reference is now made more particularly to the drawings, which illustrate the best presently known mode of carrying out the invention and wherein similar reference characters indicate the same parts throughout the views.

DETAILED DESCRIPTION OF THE DRAWINGS

Figure 1:
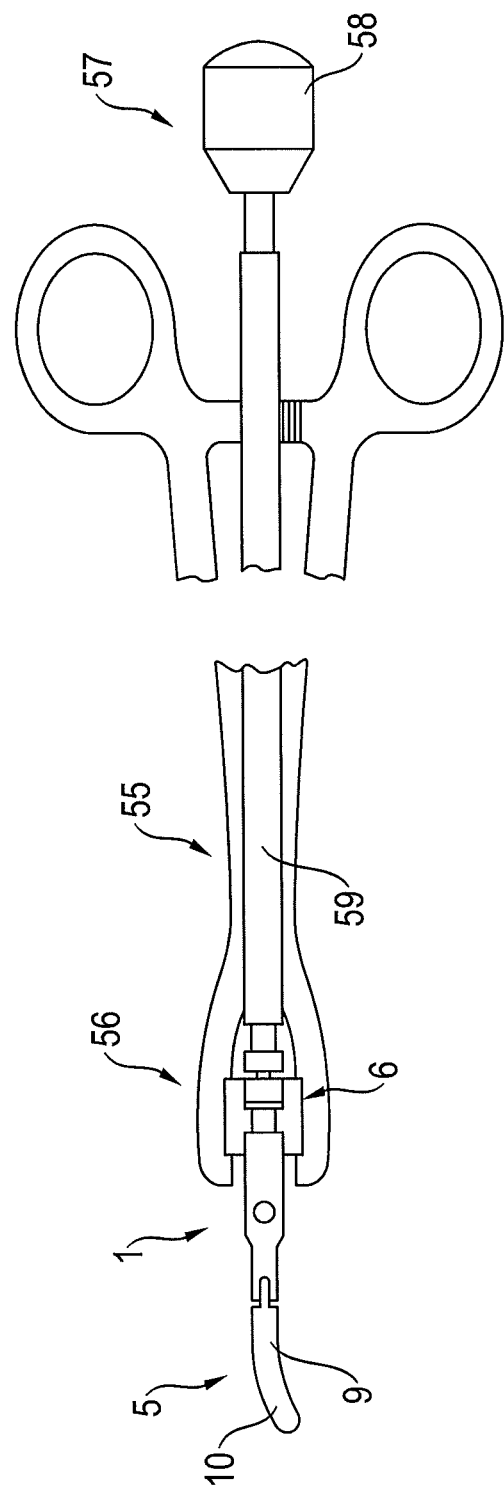
FIG. 1 is a diagrammatic view of a surgical vascular clamp from the prior art.

The surgical instrument of the prior art, indicated in a diagrammatic and basic illustration in FIG. 1 is a surgical instrument which is able to be dismantled into three components, which is disclosed in EP 2 335 609 B1. The three components form the basis of the further development. The three-part surgical instrument can be repeatably separated or respectively dismantled and completed in a simple manner between the vascular clamp 1, a supply- and removal device 54, which consists of an operating arrangement 55 and an actuating tool 57. The three components comprise an actuating tool 57 with an integrated instrument grip 58 for the opening and closing of a vascular clamp 1, an operating arrangement 55 with a gripping arrangement 58 for gripping a vascular clamp 1 and a vascular clamp 1, which comprises a coupling arrangement 6, which can be gripped by the gripping arrangement 56 arranged on the operating arrangement 55. Furthermore, there are arranged on the vascular clamp 1 an adjusting arrangement 7, a tension- and pressure element 4 and an arresting arrangement 8 (illustrated in FIG. 2), in order to enable an adjusting of the branches I, II 9, 10 of the operating means 5. The vascular clamp 1 comprises an operating means 5, consisting of two branches I, II 9, 10, which can be opened or closed by the actuating tool 57. The present invention relates to a further development of the vascular clamp 1, which on the one hand has two branches I, II 9, which are adjustable in a parallel manner to one another, and on the other hand is to correspond with the operating arrangement 55 and the actuating tool 57. This further development of the inventive vascular clamp 1 can be seen from FIG. 2. The inventive surgical vascular clamp 1 is therefore to be configured such that the ergonomically configured supply- and removal device 54 known from the prior art, consisting of an operating arrangement 55 and an actuating tool 57 with instrument grip 58 for the adjusting of the vascular clamp 1 for a simplified handling is still available to the surgeon.

Figure 2:
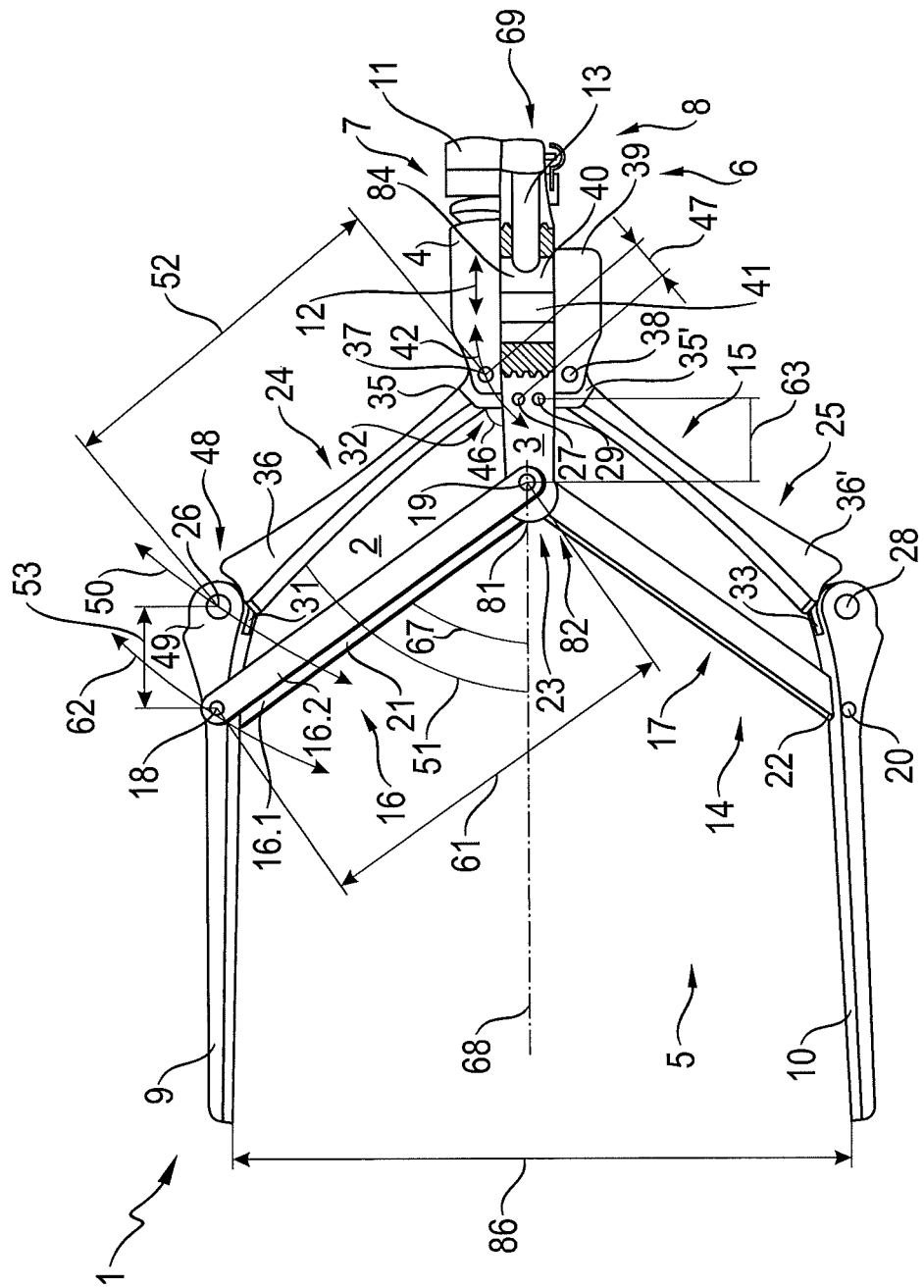
FIG. 2 is a parallel clamping embodiment of a vascular clamp according to the invention with open operating means, likewise in diagrammatic view, according to the present invention.

FIG. 2 shows in diagrammatic illustration a parallel clamping embodiment of a vascular clamp 1 according to the invention with open operating means 5. It was an object of the invention to provide a transmission of greater forces from the instrument of the vascular clamp 1 to a vessel which is to be clamped off and an opening 86 of the operating means 5, which is greater with respect to the opening of known jaw parts of "parallel clamps" from the prior art. As a solution, the operating means 5 of the vascular clamp 1 therefore has a variable opening 86 between the movable branches I, II 9, 10, which can assume a range of 0 mm to approximately 60 mm. With regard to the greater force transmission, reference is to be made to the following description concerning the embodiments of the pivot arms I, II 16, 17 and the toggle levers I, II 24, 25. The vascular clamp 1 is used as a forceps-shaped surgical instrument, which uses a mechanical procedure between its parallel branches I, II 9, 10 to press together and clamp tissues or vessels in a gentle manner. The clamping takes place by the pressure of the branches I, II 9 and 10, which is produced by the rotary movement of the adjusting element 11 on the adjusting arrangement 7. To produce the rotary movement on the adjusting element 11, an actuating tool 57 with instrument grip 58, corresponding to the embodiment according to FIG. 1 is used, the blade 60 of which is brought into engagement with the adjusting element 11. According to FIG. 1, the actuating tool 57 is guided by a hollow cylinder 59, arranged on the operating arrangement 55. The hollow cylinder 59 centres the actuating tool 57 in front of the adjusting arrangement 7 and engages with its blade 60 into an adjusting element 11 of the adjusting arrangement 7. The operating arrangement 55 grips with its gripping arrangement 56, see FIG. 1, the retaining jaws 13 of the coupling arrangement 6 of a vascular clamp 1. After each rotary movement on the actuating tool 57, a locking effect for the branch I, II 9, 10 is present via the arresting arrangement 8, in order to be able to arrest the branches I, II 9, 10 in each position. The rotary movement on the instrument grip 58 leads, via the adjusting arrangement 7, to a translatory displacement 12 of the tension- and pressure element 4 and, via the lever gear 2, ultimately to a displacement of the branch I, II 9, 10.

In order to realize a displacement of the branches I, II 9, 10, arranged in a parallel manner, a lever gear 2 according to the invention is arranged between the adjusting arrangement 7 and the branches I, II 9, 10 which are adjustable in a parallel manner. In order to enable a parallel clamping of the adjustable branches I, II 9, 10, two articulated connections 14, 15, a front 14 and a rear 15 articulated connection, are provided. The front articulated connection 14 and the rear articulated connection 15 are spaced approximately in a parallel manner. The front articulated connection 14 consists of two pivot arms I, II 16, 17, wherein the pivot arm I 16 is formed from a pair of pivot arms I 16.1, 16.2. The front articulated connection 14 is articulated via three articulation axes IV, IV', V 18, 29, 20 on the branches I, II 9, 10 and the body element 3, wherein the pair of pivot arms I 16.1, 16.2 is connected via the articulation axis IV 18 with the branch I 9 and via the articulation axis V 19 with the body element 3. The two pivot arms I 16.1, 16.2 are fastened in a rotationally movable manner respectively externally on the branch I 9 and externally on the body element 3. Thereby, the two pivot arms I 16.1, 16.2 are spaced in a parallel manner, whereby the branch I 9 and the pivot arm II 17, on closing of the operating means 5, can dip into the intermediate space between the two pivot arms I 16.1, 16.2. The pivot arm II 17, on the other hand, is connected via the articulation axis IV' 20 with the branch II 10 and via the articulation axis V 19 with the body element 3, wherein the articulation axis V 19 is the shared articulation axis V 19 of the pivot arm I 16 and of the pivot arm II 17 and is situated at the distal end 83 of the body element 3. This free end 83 of the body element 3 is constructed with a fork head 81, which receives the joint head 82 of the pivot arm II 17 in the groove 23. The pivot arm II 17, in contrast to the pivot arm I 16, is not arranged externally on the branch II 10 and is not arranged externally on the body element 3, but rather in the branch II 10 and in the body element 3. In the body element 3 and in the branch II 10 a groove 22, 23 is formed, into which the pivot arm II 17 engages and is fastened in a rotationally movable manner about the articulation axes IV', V 20, 19. The rear articulated connection 15 consists of two toggle levers I, II 24, 25, wherein the rear articulated connection 15 is articulated via four joint axes III, I, III', I' 26, 27, 28, 29 on the branches I, II 9, 10 and the body element 3. The toggle lever I 24 is connected via the articulation axis III 26 with the branch I 9 and via the articulation axis I 27 with the body element 3. This toggle lever I 24 is fastened in a rotationally movable manner on the interior on the branch I 9 and on the interior on the body element 3, about the articulation axes III, I 26, 27, because in the branch I 9 and in the body element 3 a groove 31, 32 is formed, into which the toggle lever I 24 dips. The toggle lever II 25, on the other hand, is connected via the articulation axis III' 28 with the branch II 10 and via the articulation axis I' 29 with the body element 3. This toggle lever II 25 is likewise fastened in a rotationally movable manner on the interior on the branch II 10 and on the interior on the body element 3 about the articulation axes III', I' 28, 29, because in the branch II 10 and in the body element 3 likewise a groove 33, 34 is formed, into which the toggle lever II 25 dips. The articulation axis I' 29 does not form the shared articulation axis of the toggle lever I 24 and II 25, because the toggle lever I 24 has its own articulation axis I 27 spaced from the articulation axis I' 29.

In order to bring about an adjustment of the articulated connection 14, 15 and therefore of the branches I, II 9, 10 of the operating means 5 from the actuating tool 57 via the adjusting arrangement 7 and the tension- and pressure element 4, a drive to the rear articulated connection 15 is necessary. The rear articulated connection 15 consists of two toggle levers I, II 24, 25, the embodiment of which is identical, and both toggle levers I, II 24, 25 are arranged symmetrically about a centre line 68 of the body element 3 and are therefore arranged in a mirror-inverted manner. Therefore only the technical embodiment of one toggle lever I, II 24, 25 needs to be observed and described. The description is made in a representative manner for both toggle levers I, II 24, 25, with the aid of the toggle lever I 24. The toggle lever I 24 has a long lever arm 36 and a short lever arm 35, wherein, as previously described, the toggle lever I 24 and with the short lever arm 35 is arranged on the articulation axis I 27 in the body element 3. The long lever arm 36 of a toggle lever I 24 has at the free end a joint head 48 with an eye, whilst on the short lever arm 35 a spring 85 is arranged, having two openings for receiving two articulation axes I, II 27, 37. Furthermore, a further articulation axis II 37 is situated in the short lever arm 35. The tension- and pressure element 4 is connected to this articulation axis II 37, whereby the connection to the instrument grip 58 of the actuating tool 57 is produced. Therefore, a continuous connection is produced from the screw/nut drive, consisting of the actuating tool 57, the adjusting element 11 and tension- and pressure element 4, to the lever gear 2, whereby a rotary movement is converted or respectively transferred into a linear displacement 12.

As the toggle lever II 25 is constructed in a mirror-inverted manner to the toggle lever I 24, the connection of the toggle lever II 25 to the body element 3 is to be regarded in an analogous manner to the toggle lever I 24. The toggle lever II 25 has a long lever arm 36' and a short lever arm 35', wherein, as previously described, the toggle lever II 25 and therefore the short lever arm 35' is arranged on the articulation axis I' 29 in the body element 3. Furthermore, a further articulation axis II' 38 is situated in the short lever arm 35'. A push-pull rod 39 is connected to this articulation axis II' 38. The short lever arm 35' of the toggle lever II 25 engages with its joint head 80 in the fork head 79 of the push-pull rod 39, which are arranged rotatably about a shared articulation axis II' 38.

In order to produce a connection to the instrument grip 58 of the actuating tool 57, it is necessary to produce a connection between the push-pull rod 39 and the tension- and pressure element 4. Only thereby would a continuous connection from the screw/nut drive to the complete lever gear 2 be ensured. In order to fulfil this requirement, the body element 3 has a slot 40 in the form of a groove, which penetrates the body element 3. Through this slot 40 a connecting element 41 is guided, which connects the tension- and pressure element 4 with the push-pull rod 39. The connection between the tension- and pressure element 4 and the push-pull rod 39 is a fixed connection which is not detachable. A continuous connection from the instrument grip 58 of the actuating tool 57 to the toggle lever II 25 of the lever gear 2 only exists with the connecting element 41. This is possible, because a fixed connection exists between the tension- and pressure element 4 and the push-pull rod 39 through the connecting element 41. If the tension- and pressure element 4 is displaced in a translatory manner, the push-pull rod 39 simultaneously moves linearly along the body element 3. The slot length 84 of the slot 40 therefore amounts to at least the length of the linear displacement 12 of the tension- and pressure element 4.

In order to enable a parallel clamping of the displaceable branches I, II 9, 10, in the fork-like shaping at the end of the tension- and pressure element 4 the short lever arm 35 of a toggle lever I 24 is articulated via an articulation axis II 37. The same applies to the toggle lever II 25, the short lever arm 35' of which is articulated in a fork-like shaping at the end of the push-pull rod 39 via an articulation axis II' 38. The articulation axis II, II' 37, 38 is constructed respectively as a pivot bearing and is displaced by the tension- and pressure element 4, and by the push-pull rod 39 on a length b, wherein b is the radian on a circular arc 42. For reasons of clarity, the circular arc 42' about the articulation axis II' 38 is not entered in the drawing, because the circular arc 42' is identical to the circular arc 42. As the movements of the branch I 9, of the pivot arm I 16, of the toggle lever I 24 and of the tension- and pressure element 4 are identical to the movements of the branch II 10, of the pivot arm II 17, of the toggle lever II 25 and of the push-pull rod 39, the description of the lever gear 2 is made by means of the movements of the branch I 9, of the pivot arm I 16, of the toggle lever I 24 and of the tension- and pressure element 4. The following description of the mode of operation and of the technical embodiment of the lever gear 2 is therefore made by means of the levers 9, 16, 24, 4, wherein the description is to be applied in an analogous manner to the levers 10, 17, 25, 39. For the levers 16, 17, 24, 25, 4, 39, the base of the lever gear 2 is the body element 3, on which all components, including adjusting element 7, coupling arrangement 6 and arresting arrangement 8 are arranged.

A displacement of the articulation axis 37 on the circular arc 42 is alternating owing to a straight-lined forward and backward displacement 12 of the tension- and pressure element 4. Furthermore, the short lever arm 35 of the toggle lever I 24 is fastened on the body element 3 via an articulation axis I 27. The body element 3 is divided into three functional regions I, II, III 43, 44, 45, which are described in further detail in FIG. 3. The short lever arm 35 of the toggle lever I 24 is pivotably arranged about an angle α 46 about the articulation axis I 27, which is constructed as a pivot bearing. The legs of the angle α 46 are formed by the body element 3 and the short lever arm 35. The angle range of the angle α 46 is determined by the axis distance I 47 which results from the distance of the articulation axis I 27 on the body element 3 to the articulation axis II 37 on the short lever arm 35 or respectively the tension- and pressure element 4 and via the path length s of the linear displacement 12, which results from the straight-lined displacement of the tension- and pressure element 4. The same or respectively comparable applies to the angle range α' (not illustrated, for reasons of clarity, but analogous to 46), which is likewise determined by an axis distance (not illustrated, but which is analogous to I 47). The axis distance results from the distance of the articulation axis I' 29 on the body element 3 to the articulation axis II' 38 on the short lever arm 35' or respectively the push-pull rod. 39 and via the path length s of the linear displacement 12, which results from the straight-lined displacement of the tension- and pressure element 4.

The axis distance I 47 corresponds to the radius r from the rotation point of the articulation axis I 27 up to the circular arc b, on which the articulation axis II 37 moves. The angle ϑ, which is proportional to the angle α 46, results from the radius r and the radian b, which corresponds approximately to the path length s 12 of the linear displacement 12 of the tension- and pressure element 4. The angle ϑ is not illustrated in FIG. 2 for reasons of clarity.

The bent long lever arm 36 adjoins onto the short lever arm 35 of the toggle lever I 24. The angle between the short and the long lever arm 35, 36 of the toggle lever I 24, which, also fulfils the function of a joint lever, lies in an angle range of approximately 120 degrees to 150 degrees and is preferably approximately 135 degrees. The tension- and pressure element 4 and the toggle lever I 24, which can be pivoted about a particular angle range by the tension- and pressure element 4, are part of the lever gear 2. A joint head 48 with an eye is situated at the end of the toggle lever I 24. The joint head 48 dips into the fork head 49 of the displaceable branch I 9. The joint head 48 and the fork head 49 are connected with one another in a rotationally movable manner via a shared articulation axis III 26. On the displacement of the articulation axis II 37, also simultaneously the toggle lever I 24 is displaced with its articulation axis III 26. The displacement of the articulation axis III 26 takes place likewise on a circular arc 50. The extent of the displacement of the articulation axis III 26 on the circular arc 50 or respectively also its delimitation in the displacement, is determined by the displacement of the articulation axis II 37 and the pivoting of the toggle lever I 24 about the rotation point of the articulation axis I 27. The displacement of the toggle lever I 24 takes place about a particular angle β 51 in a particular angle range, which is produced from the legs of the body element 3 and the long lever arm 36 of the toggle lever I 24. The angle range lies approximately between 5 degrees and 70 degrees and is preferably approximately 60 degrees. The angle range of the angle β 51 is determined by the axis distance II 52, which results from the distance of the articulation axis II 37 to the articulation axis III 26 on the long lever arm 36 and the axis distance I 47 between the articulation axis II 37 and the articulation axis I 27 on the short lever arm 35, and by the path length s of the linear displacement 12, which results from the straight-lined displacement of the tension- and pressure element 4 and the displacement of the toggle lever I 24 about the angle ϑ.

The displaceable branch I 9 has a further articulation axis IV 18, spaced apart from the articulation axis III 26 over a particular axis distance III 53. This articulation axis IV 18 is the shared articulation axis IV 18 for the pivot arms I 16.1, 16.2 arranged in a rotationally movable manner on the branch I 9. Owing to the side view, only the front pivot arm 16.1 is readily visible, whilst the rear pivot arm 16.2 is largely concealed. The pivot arms I 16.1, 16.2' concern a pair of pivot arms I 16, which are arranged on the one hand on the side faces of the branch I 9 and on the other hand on the side faces of the body element 3. This means that on each side face of the branch I 9 and of the body element 3 a pivot arm I 16.1, 16.2 is arranged, respectively spaced by the cross-section of the branch I 9 or respectively of the body element 3. The upper end of the pivot arm I 16 is arranged in a rotationally movable manner on the branch I 9 about the articulation axis IV 18 and the lower end of the pivot arm I 16 is arranged in a rotationally movable manner on the body element 3 about the articulation axis V 19. The articulation axis IV 18 and the articulation axis V 19 form a particular axis distance IV 61. The axis distance IV 61 is designed structurally such that the displaceable branch I 9 is always in a substantially parallel state with respect to the displaceable branch II 10. On the displacement of the branch I 9 by the toggle lever I 24, the branch I 9 is positively guided via the connection of the pivot arms I 16.1, 16.2 to the body element 3. Owing to this positive guidance by the pivot arms I 16.1, 16.2, the displaceable branch I 9 always remains in a parallel position to the displaceable branch II 10. In order to be able to fulfil this requirement of the parallel position of the displaceable branch I 9 to the displaceable branch II 10 in every open and closed position, the pivot arms I 16.1, 16.2 must be arranged in a rotationally movable manner about the rotation point of the articulation axis V 19 and about the rotation point of the articulation axis IV 18, wherein the articulation axis V 19 has a particular axis distance 61 from the articulation axis I 27 arranged in the body element 3.

The displacement of the articulation axis III 26 by the toggle lever I 24 brings about a simultaneous displacement of the articulation axis IV 18. The displacement of the articulation axis IV 18 takes place likewise on a circular arc 62. The extent of the displacement of the articulation axis IV 18 on the circular arc 62 or respectively also its delimitation in the displacement, is determined by the displacement of the articulation axis II 37 and therefore of the toggle lever I 24 and by the pivoting of the toggle lever I 24 about the rotation point in the articulation axis I 27. So that a parallel displacement of the branch I 9 to the branch II 10 can take place, the circular arc 62 must have the same size as the circular arc 50. The displacement of the articulation axis III 26 on the circular arc 50 and the displacement of the articulation axis IV 18 on the circular arc 62 must take place simultaneously and spaced in a parallel manner with respect to one another. Both articulation axes IV 18 and III 26 must cover simultaneously the same path on the circular arcs 50, 62, only thereby is the parallel position of the branch I 9 to the branch II 10 maintained. The long lever arm 36 of the toggle lever I 24 and the short lever arm 35, however, are not spaced in a parallel manner to the pivot arms I 16.1, 16.2. The opposite sides, the pivot arms I 16.1, 16.2 and the toggle lever I 24 therefore do not run parallel. This arrangement concerns an antiparallelogram by which straight-lined movements are converted into circular movements. Compared to a parallelogram with four corner points, the mechanical construction of the lever gear 2 with rigid sides and joints at the corner points has, however, five articulation axes 18, 19, 26, 27, 37, from which also five axis distances I 47, II 52, III 53, IV 61, V 63 result. The axis distance I 63 results from the distance of the articulation axis V 19 to the articulation axes I, I' 27, 29. The same applies to the mirror-inverted articulation axes 19, 20, 28, 28, 38 of the lever gear 2, which also have five axis distances (not illustrated). The lever gear 2 comprises in total, however, only nine articulation axes 18, 19, 20, 26, 27, 28, 29, 37 and 38, because the articulation axis V 19 is used jointly by the pivot arm I 16 and by the pivot arm II 17.

Five axis distances I 47, II 52, III 53, IV 61, V 63 form simultaneously five sides which correspond in the broadest sense to the typical house shape of a traditional German "Staudenhaus" farmhouse. Only the axis distance V 63 between the articulation axis V 19 and the articulation axis I 27 and the axis distance V 53 between the articulation axis IV 18 and the articulation axis III 26 are identical, all other axis distances I 47, II 52, IV 61 are unequal. As, however, the branches I, II 9, 10, which are spaced with respect to one another are to move closer to one another (towards one another) or further from one another (away from one another) in a parallel manner, the toggle lever I 24 according to the invention is formed structurally such that the two different movements, which the toggle lever I 24 carries out simultaneously about its articulation axis I 27 and its articulation axis II 37, lead to a resulting movement. Owing to this resulting movement of the toggle lever I 24, the articulation axes IV 18 and III 26 can carry out a consistent circular movement or respectively displacement on the circular arcs 50, 62. This previously indicated description is to be applied in an analogous manner for the branch II 10, the pivot arm II 17, the toggle lever II 25, the push-pull rod 39 and of the body element 3.

Figure 3:
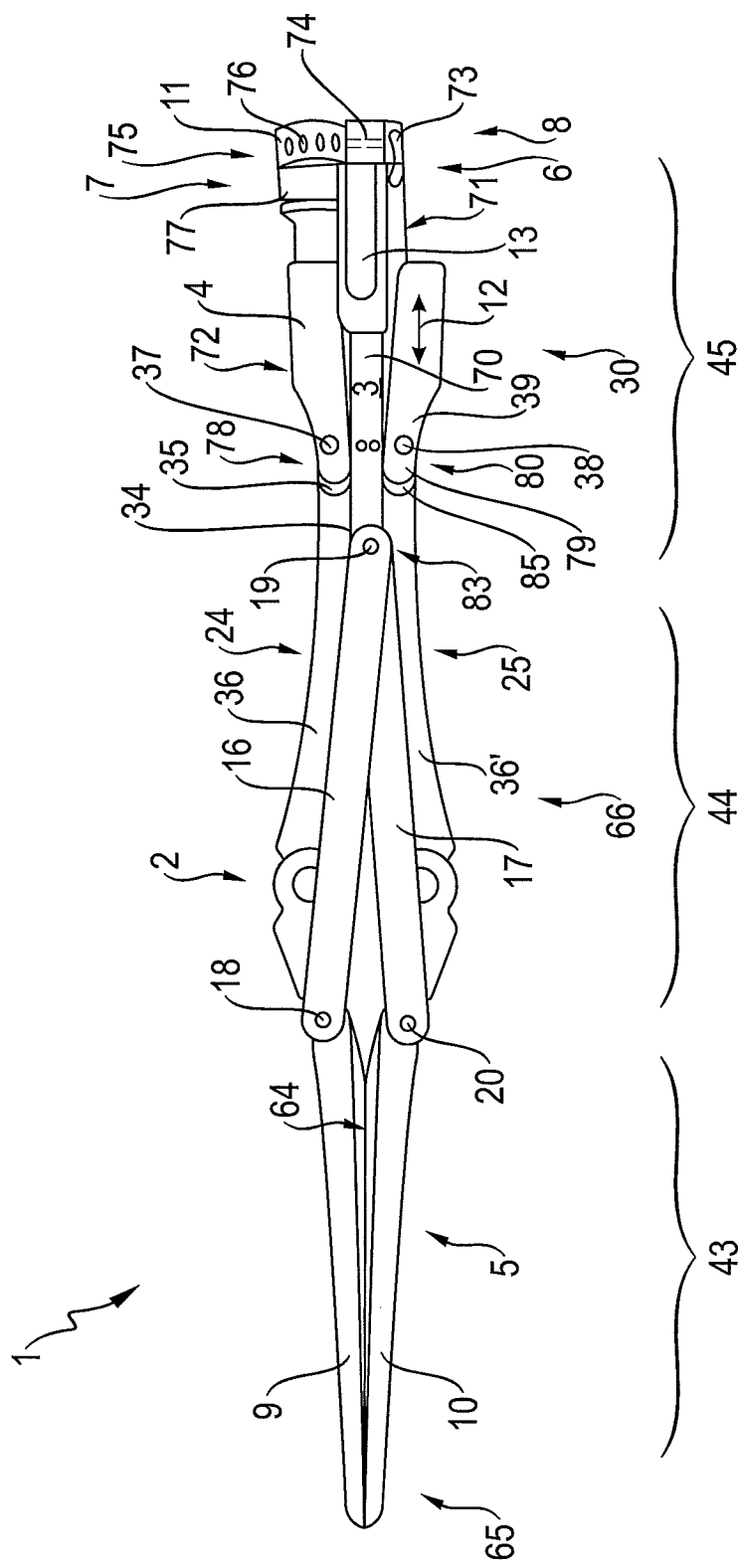
FIG. 3 is a parallel clamping embodiment of a vascular clamp according to the invention, with closed operating means in perspective side view, according to the present invention.

FIG. 3 shows a parallel clamping embodiment of a vascular clamp 1 according to the invention with closed operating means 5. From the perspective side view, the supporting body element 3 can be seen with the embodiments of the lever gear 2 according to the invention. The reference numbers presented in FIG. 2 are taken over here in an analogous manner, but are not described in further detail. Furthermore, reference numbers from FIG. 3 can be specified in FIG. 2. Basically, the vascular clamp 1 has three functional regions I, II, III 43, 44, 45. The three functional regions I, II, III 43, 44, 45 relate to an operating means 5 in the functional region I 43, a lever gear 2 in the functional region II 44 and a carrier part 30 in the functional region III 45.

The operating means 5 from the functional region I 43 has two displaceable branches 9, 10, which in the closed state form at the free distal end 65 an oval cross-section. The central part 66 of the functional region II 44 has the lever mechanism of the lever gear 2, consisting of two pivot arms 16, 17, which are connected via articulation axes 18, 20 with the branches 9, 10 and via an articulation axis 19 with the body element 3 and consisting of two toggle levers 24, 25, which are connected via articulation axes 26, 28 with the branches 9, 10 and via the articulation axes 27, 29 with the body element 3. The carrier part 30 has a tension- and pressure element 4 and a push-pull rod 39, which are connected with the toggle levers 24, 25 via the articulation axes 37, 38.

The first functional region I 43, which presents the operating means 5 of the vascular clamp 1 is formed from two branches I, II 9, 10, which respectively have a toothing 64. The toothing 64 of the branches I, II 9, 10 terminates at the free end, the distal end 65 of the vascular clamp 1. The adjustable branches I, II 9, 10 arranged in the functional region I 43 have a shape which runs in a relatively straight-lined and tapering manner towards the distal end 65. The length of the functional region I 43 is approximately ⅓ of the total length of the vascular clamp 1. On the face side, the freely standing distal end 65 of the approximately oval cross-section of the branches I, II 9, 10 is rounded.

The second functional region II 44 consists of the central part 66, wherein the length of the functional region II 44 is approximately ⅓ of the total length of the vascular clamp 1. The central part 66 no longer contains any toothing 64, but receives a portion of the lever mechanism of the lever gear 2 according to the invention. The lever mechanism in the central part 66 of the vascular clamp 1 consists of a pivot arm II 17 and of a pair of articulated pivot arms I 16. The pivot arms I 16.1, 16.2 are spaced in a parallel manner and extend in the same direction as the pivot arm II 17, etc. from the branch I 9 towards the body element 3. The pivot arm pair I 16 or respectively each of these pivot arms I 16.1, 16.2 is arranged in the central part 66 of the vascular clamp 1 on the side face of the free end 83 of the body element 3, whilst the pivot arm II 17 is arranged in a rotationally movable manner at the free end 83 of the body element 3 in a fork-shaped recess (groove 23). The central part 66 of the vascular clamp 1 has at a corresponding site an articulation axis IV, IV' 18, 20, about which the two pivot arms I, II 16, 17 are pivotable about an angle γ 67 (see FIG. 2). When the operating means 5 is closed, as shown here, the two branches I, II 9, 10 lie directly one over another and the free ends of the branches I, II 9, 10 at the distal end 65 are congruent. This is only possible because the two pivot arms I 16.1, 16.2 can partially receive between them a portion of the pivot arm II 17. The angle γ 67 between the leg of the pivot arm I, II 16, 17 and the extended centre line 68 of the body element 3 is approximately 5 to 10 degrees, preferably 8 degrees, in the closed position of the operating means 5.

The other free end of the body element 3 lies at the proximal end 69 in the functional region III 45, which is constructed as carrier part 30. The length of the functional region III 45 is approximately ⅓ of the total length of the vascular clamp 1. The carrier part 30 has an approximately rectangular cross-section, whilst the cross-section at the distal end 65 with closed branches I, II, 9, 10 is approximately square. The cross-section at the proximal end 69 of the carrier part 30, on the other hand, has a rectangular cross-section, which is approximately three to four times as great as the cross-section at the distal end 65 of the branches I, II 9, 10. Owing to the rectangular cross-section, four sides are present with respectively a plane face, two side faces 70, a face on the underside 71 and one on the upper side 72. The carrier part 30 has a retaining jaw 13 respectively at the two side faces 70 which are spaced in a parallel manner and at the proximal end 69 of the body element 3. The two retaining jaws 13, spaced in a parallel manner and lying opposite one another, are connected in one piece with the carrier part 30 and therefore with the body element 3. The retaining jaws 13 form the coupling means of the coupling arrangement 6. Furthermore, an arresting arrangement 8 is situated in the functional region III 45 at the proximal face end 69. The arresting arrangement 8 is formed from a leaf spring 73, which is arranged on the underside 71 of the carrier part 30, and of an arresting pin 74, guided in a bore, which arresting pin engages into a detent profile 75 arranged in an adjusting element 11. The detent profile 75 in the adjusting element 11 basically consists of indicated bores 76, arranged in a row adjacent to one another, of small depth or respectively small centerings.

On the upper side 72 of the body element 3 there is situated in the functional region III 45, adjoining onto the adjusting element 11, a mount 77, which is connected on the one hand in one piece with the carrier part 30 and on the other hand receives the tension- and pressure element 4 and therefore forms the adjusting arrangement 7. The tension- and pressure element 4 is constructed in a fork-like manner at the end of the side facing away from the mount 77. The fork head 78 receives the upper end of the short lever arm 35 of the toggle lever I 24, whilst the lower end of the short lever arm 35 engages in a groove 32 let into the upper side 72 of the body element 3 (see FIG. 2). The lower end of the lever arm 35, let into the body element 3, is fastened in a rotationally movable manner on an articulation axis I 27, whilst the upper end of the lever arm 35 is connected in a rotationally movable manner on an articulation axis II 37 with the tension- and pressure element 4. When the tension- and pressure element 4 and therefore also the push-pull rod 39 has covered the maximum path length s of the linear displacement 12 in forward direction and has pivoted and pushed the toggle levers I, II 24, 25 forwards, the displaceable branches I, II 9 and 10 are situated in their closed final position. In the final position of the toggle levers I, II 24, 25, the angle β 51 (see FIG. 2) between the legs of the long lever arms 36, 36.1 of the toggle levers I, II 24, 25 and the extended centre line 68 of the body element 3 is approximately between 5 to 8 degrees and the branches I, II, 9, 10 which are displaceable in a parallel manner, lie against one another. When the tension- and pressure element 4 and therefore also the push-pull rod 39 has covered the maximum path length s 28 in backward direction and has pivoted back and drawn back the toggle levers I, II 24, 25, the displaceable branches I, II 9, 10 are situated in their almost maximum opened final position, see FIG. 2. Of course, the branches I, II 9, 10, which are displaceable in a parallel manner, can also take up any position between the maximum opened final position and the closed final position, for the clamping of tissue. Any other clamping position taken up between the final positions can be fixed by means of the arresting arrangement 8.

LIST OF REFERENCE NUMBERS 1 vascular clamp
2 lever gear
3 body element
4 tension- and pressure element
5 operating means
6 coupling arrangement
7 adjusting arrangement
8 arresting arrangement
9 branch I
10 branch II
11 adjusting element
12 linear displacement (path s)
13 retaining jaw
14 articulated connection (front)
15 articulated connection (rear)
16 pivot arm I
17 pivot arm II
18 articulation axis IV (of 9, 16)
19 articulation axis V (of 3, 16, 17)
20 articulation axis IV' (of 10, 17)
21 intermediate space
22 groove (in 10)
23 groove (in 3) I
24 toggle lever I
25 toggle lever II
26 articulation axis III (of 9, 24)
27 articulation axis I (of 3, 24)
28 articulation axis III' (of 10, 25)
29 articulation axis I' (of 3, 25)
30 carrier part
31 groove (in 9)
32 groove II (in 3)
33 groove (in 10)
34 groove III (in 3)
35, 35' lever arm (short)
36, 36' lever arm (long)
37 articulation axis II (in 4,35)
38 articulation axis II' (39,35.1)
39 push-pull rod
40 slot IV (groove in 3)
41 connecting element (betwn. 4, 39)
42 circular arc (around 37, 38)
43 functional region I
44 functional region II
45 functional region III
46 angle range α (between 3 and 35)
47 axis distance I (of 27, 37)
48 joint head (of 24, 36)
49 fork head (of 9)
50 circular arc (around 26, 28)
51 angle range β (between 3 and 24)
52 axis distance II (of 26,37)
53 axis distance III (of 18,26)
54 supply- and removal device
55 operating arrangement
56 gripping arrangement
57 actuating tool
58 instrument grip
59 hollow cylinder
60 blade
61 axis distance IV (of 18,19)
62 circular arc (around 18,20)
63 axis distance V (of 19,27)
64 toothing
65 distal end (of 1)
66 central part
67 angle range γ (betwn. 3 & 16)
68 centre line (of 1,3,)
69 proximal end (of 1)
70 side face
71 underside
72 upper side
73 leaf spring
74 arresting pin
75 detent profile
76 bore
77 mount
78 fork head (of 4)
79 fork head (of 39)
80 joint head (of 25,35.1)
81 fork head (of 3)
82 joint head (of 17)
83 free end (of 3)
84 slot length
85 spring (of 35, 35')
86 opening (of 5)

The invention claimed is:

1. A surgical instrument for use as a minimally invasive, continuously gripping and clamping vascular clamp which is suitable for the occluding of tube shaped organic body parts, the instrument comprising:
a lever gear formed as an elongate, L-shaped body element having a rectangular cross section, the body element including:
a first groove forming a fork head arranged at a free distal end of the body element;
a second groove located on an upper side of the body element;
a third groove boated on a lower side of the body element and parallel to the second groove and perpendicular to a center line;
a fourth groove formed as a slot spaced apart from the free distal end that penetrates into the body element from the upper side of the body element to the lower side of the body element and running in a direction perpendicular to the center line, and wherein the fourth groove has a slot length;
three articulation axes, a first axis of the three articulation axes arranged in the first groove, a second axis of the three articulation axes arranged in the second groove, and a third axis of the three articulation axes arranged in the third groove, the first, second, and third articulation axes perpendicular to the fourth groove;
an axially displaceable tension and pressure element having a fork-like formation and an axially displaceable push-pull rod having a fork-like formation arranged and displaceable along a center line of the body element above and below the body element and spaced in a parallel manner from one another and securely connected with one another via a connecting element, and wherein the slot length of the slot corresponds to a path length of the tension and pressure element, and the slot is used to guide the connecting element;

two articulating toggle levers arranged above and below the body element and connected at a first end to the body element formed from a bent lever and each having: a short lever arm with a spring arranged thereon and a long lever arm, wherein the fork-like formations of the tension and pressure element and the push-pull rod each receive a corresponding toggle lever of the two articulating toggle levers and the spring of the short lever arm of the corresponding toggle lever:

two articulating pivot arms arranged above and below the body element and connected at a first end to the body element distal to the connection between the first ends of the toggle levers and the body element, wherein the first pivot arm includes a pair of connection members connected to the body element opposite the second pivot arm;

a coupling arrangement arranged at a proximal end of the body element including:

two retaining jaws for receiving a detachable supply and removal device which is able to be operated by a surgeon;

an adjusting arrangement in combination with an arresting arrangement, both located at the proximal end of the body element;

wherein the connection of the pivot arms and toggle levers runs perpendicularly to the coupling arrangement;

an operating means at a distal end of the body element with two atraumatic branches spaced longitudinally and parallel to the body element and connected with the body element via a front parallelogram-shaped articulation joint with three joint axes comprising the pivot arms and a rear parallelogram-shaped articulation joint with four axes comprising the toggle levers in a rotationally movable manner at the free end of the body element which are able to be actuated relative to one another from a completely open position into a completely closed position;

wherein the adjusting arrangement serves to receive a detachable actuating tool capable of rotary movement and wherein when the actuating tool is moved in a rotational direction along the center line, the adjusting arrangement in connection with the tension and pressure element causes axial displacement of the tension and pressure element and push-pull rod to cause opening and closing the movable branches which are adjustable continuously in a parallel manner with respect to one another.

2. The surgical instrument according to claim 1, wherein a first articulation axis of the three articulation axes receives the two pivot arms outside the fork head spaced apart in parallel through a cross section of the branches and the body element outside the fork head, thus immersing the pivot arm during closure of the operating means in an intermediate space thereof.

3. The surgical instrument according to claim 1 wherein linear displacement of the tension and pressure element and the push-pull element on the path length results in an angular displacement of the second articulation axes and the third articulation axes in a first angle range and an angular displacement of two of three joint axes of the pivot arms with the movable branches in a second angle range.

4. The surgical instrument according to claim 1, wherein the arresting arrangement at the proximal end of the body element includes a leaf spring arranged on an underside of the body element and an arresting pin guided in a bore which engages with a latching profile arranged in an adjustment element, wherein the latching profile is made up of bores lined up alongside one another.

* * * * *

UNITED STATES PATENT AND TRADEMARK OFFICE
CERTIFICATE OF CORRECTION

PATENT NO. : 10,398,446 B2  
APPLICATION NO. : 14/874515  
DATED : September 3, 2019  
INVENTOR(S) : Wolfgang Wiedenbein Page 1 of 1

It is certified that error appears in the above-identified patent and that said Letters Patent is hereby corrected as shown below:

In the Claims

In Column 30, Line 45, delete "boated" and replace with -- located --

Signed and Sealed this  
First Day of December, 2020

Andrei Iancu  
*Director of the United States Patent and Trademark Office*